US006825394B1

(12) United States Patent
Rudland et al.

(10) Patent No.: US 6,825,394 B1
(45) Date of Patent: Nov. 30, 2004

(54) CONDITIONALLY IMMORTALIZED CELL LINES DERIVED FROM TRANSGENIC ANIMALS

(76) Inventors: Philip Spencer Rudland, c/o Department of Biological Sciences, The University of Liverpool L69 3BX, Liverpool (GB); Barry Roger Barraclough, Department of Biological Sciences, The University of Liverpool L69 3BX, Liverpool (GB); Iain Charles Kilty, Department of Biological Sciences, The University of Liverpool L69 3BX, Liverpool (GB); Barry Robert Davies, Addenbrooks Hospital, P.O. Box 238, Cambridge (GB), CB2 2QQ; Guenter Schmidt, 13 Station Road CB1 2JB, Cambridge (GB)

( * ) Notice: Subject to any disclaimer, the term of this patent is extended or adjusted under 35 U.S.C. 154(b) by 0 days.

(21) Appl. No.: 09/173,821

(22) Filed: Oct. 16, 1998

Related U.S. Application Data

(63) Continuation of application No. PCT/GB97/01063, filed on Apr. 17, 1992.

(30) Foreign Application Priority Data

Apr. 17, 1996 (GB) ............................................. 9607953

(51) Int. Cl.[7] ...................... A01K 67/027; A01K 67/00; C12N 15/00; C12N 15/63; G01N 33/00
(52) U.S. Cl. ................................ 800/14; 800/3; 800/8; 800/10; 800/13; 800/18; 800/21; 800/25; 435/69.1; 435/320.1; 435/325; 435/455
(58) Field of Search ............................ 800/3, 8, 10, 13, 800/14, 18, 21, 25; 435/69.1, 320.1, 325, 455; 536/23.1

(56) References Cited

U.S. PATENT DOCUMENTS 5,087,571 A * 2/1992 Leder et al. .............. 435/240.2
5,489,742 A * 2/1996 Hammer et al. ................ 800/2

FOREIGN PATENT DOCUMENTS

| EP | 0169672 | 6/1985 | | |
|---|---|---|---|---|
| WO | 8909816 | 10/1989 | | |
| WO | 9113150 | 9/1991 | | |
| WO | WO 91/13150 | * | 9/1991 | ........... C12N/15/00 |
| WO | 9210563 | 6/1992 | | |
| WO | 9511308 | 4/1995 | | |

OTHER PUBLICATIONS

Yazdanbakhsh et al. Nuc. Acid. Res. 21(3):455–61, 1993.*
Wall RJ Theriogenology 45:57–68, 1996.*
Moses JH Br. J. Cancer. 69(21):1, 1994.*
Stocklin et al (J. Cell Bio. 122(1):199–208, 1993.*
Reeben et al Biochem. Biophy. Res. Com. 192(2):465–470, 1993.*
"Tissue–Specific Expression of Rat Light Neurofilament Promoter–Driven Reporter Gene in Transgenic Mice" by Reeben et al.; Biochemical and Biophysical Research Communications, pp. 465–470; XP002034398, vol. 192, No. 2, Apr. 30, 1993.
"Glucocorticoid Regulation of Mouse Mammary Tumor Virus Sequences in Transgenic Mice" by Ross et al.; Proc. Natl. Acad. Sci. USA; vol. 82, pp. 5880–5884; Sep. 1985; Genetics.
"Normal and Neoplastic Mammary Glands MMTV/TGF α Transgenic Mice" by Mizuno et al.; in vivo vol. 8; pp. 263–270 (1994).
Database WPI, Section Ch, Week 9145, Derwent Publications, Ltd., London, GB; Class B04, AN 91–329070; XP002034463 and JP 03 219 821 A (Snow Brand Milk Prod. Co., Ltd.); Sep. 27, 1991.
"Single–Step Induction of Mammary Adenocarcinoma in Transgenic Mice Bearing the Activated c–neu Oncogene" by Muller et al., Ceil. vol. 54, pp. 105–115, Jul. 1, 1988.

* cited by examiner

*Primary Examiner*—Jeffrey Fredman
*Assistant Examiner*—Sumesh Kaushal
(74) *Attorney, Agent, or Firm*—Baker Botts L.L.P.

(57) ABSTRACT

The invention relates to mammalian cell lines and transgenic mammals. More particularly, it relates to a method for producing a rat cell line, a method for producing a transgenic rat, a transgenic rat, a rat cell line, cells and tissue obtained therefrom and uses therefore. The cell line derived from a transgenic mammal comprises: (i) a conditional oncogene, transforming gene or immortalising gene or a cell cycle affecting gene; and (ii) a cell type specific promoter. They include a neuronal cell line in which the cell type specific promoter is an NF-L gene promoter, and a mammary cell line in which the cell type specific promoter is a MMTV gene promoter. The conditional oncogene, transforming gene or immortalising gene is preferably a SV40tsA58 gene.

11 Claims, 13 Drawing Sheets

Neuro-specific enolase:
46kD

A   B   D

Synaptophysin:
38kD

A   B   C   D

MAP2:
280kD

~90kD
~80kD

A   B   C   D

Tau:
~60kD

A   B   C   D

Neurofilament:
68kD 
~55kD

A   B   C   D

GFAP (Glial cell marker): 51kD

A   B   C   A   B   D

CONDITIONALLY IMMORTALIZED CELL LINES DERIVED FROM TRANSGENIC ANIMALS

This is a continuation of copending International Appln. PCT/GB97/01063 filed Apr. 17, 1997.

The present invention relates to cell lines and transgenic animals. More particularly it relates to a method for producing a rat cell line, a method for producing a transgenic rat, a transgenic rat, a rat cell line, cells and tissue obtained therefrom and uses therefore.

Currently there are few permanently growing or immortalised cell lines of epithelial or neuronal origin which are fully characteristic of the differentiated phenotype or produce differentiated products at the levels seen in viva. For example, there are immortalised cell lines of human and rodent origin from the breast but these fail to express many of the characteristics of fully differentiated cells in vivo (Cancer Metastasis Rev. 6. 55–83, 1987 and Histol, Histopathol. 8 385–404, 1993). Those of the Central Nervous System (CNS) have limited proliferation capabilities whilst those that do proliferate are almost exclusively derived from neuroblastomas of peripheral nerves and are not representative of the CNS.

The present in vitro methods for examining differentiated epithelial and neuronal cell behaviour involves repeated establishment of primary cell cultures from rodent fetal tissues. Unfortunately these cultures rapidly senesce, contain mixed populations of cells and invariably are overgrown by contaminating, more rapidly growing cell types such as fibroblasts (J. Cell Biol. 73. 561–577, 1977 and In Vitro, 25, 23–36, 1989). They are therefore unsuitable for most molecular analyses where total cell extracts are required such as, for example, assays for messenger RNA, specific proteins, ligand-receptor interactions, and are wasteful in time and animals used for their production. The ability to produce immortalised populations of such cells would therefore be an enormous advantage for basic and applied biological studies. Since the rat is the laboratory animal used in most pharmacological studies, it is the animal of choice for any experimentally-derived cell systems for the pharmaceutical and toxicological industries.

Unfortunately the very process of immortalisation or transformation mitigates against the expression of the differentiated phenotype, since biological systems are almost invariably programmed only to differentiate after proliferation has ceased. Thus primary cultured cells, if they can be induced to proliferate, may be immortalised by chemical agents or more specifically by transforming or immortalising genes carried by oncogenic viruses (J. Virol 15., 613–618, 1985) eg. breast cells. (Dev. Biol. 136 167–180, 1989), but the resultant cell lines fail to express the levels of differentiated products or structures seen in vivo (Histol, Histopathol. 8, 385–404, 1993, J. Cell Biol. 91., 827–836, 1981, Eur.J. Biochem. 133, 707–715, 1983, J. Natl. Cancer Inst. 76, 246–256, 1986). If the primary cultures do not possess much ability to proliferate (eg. neuronal cells) then introduction of immortalising genes, by whatever route, fails to immortalise the cells, since several rounds of replication of the DNA are required to integrate successfully any transfected DNA into that of the host (J. Virol 15, 613–618, 1975).

There are essentially two approaches to the generation of cell lines.

1) One can isolate primary tissue cells from the tissue of interest and culture these in vitro. One can then attempt to immortalise these cells in vitro using various techniques before they senesce, using microinjection or other transfection techniques.

2) One can attempt to generate a transgenic animal from which to derive cell lines.

Primary Cell Transfection:

The most common way of immortalising primary tissue cells is to transform these with an immortalising gene construct. Such genes are commonly found in a variety of viruses. There are various problems with this technique. One needs a large number of primary cells as transformation is inefficient. Transformation will result in integration of the transforming construct into arbitrary sites in the genomic DNA. The genomic environment of the integration determines its levels of expression and experience shows that this tends to be highly variable so transformations of the same primary tissue often give rise to cell lines with widely differing properties. The immortalisation of cells also tends to suppress terminal differentiation which is disadvantageous if the cell line is supposed to mimic the behaviour of its tissue of origin.

One can use a conditional immortalising gene construct. An example is a temperature sensitive mutant, tsA58 (P. Tegtmeyer, J. Virol. 15, 613–618, 1975) which is found in the early region of the Simian Virus 40, and which encodes a thermolabile protein, the Large Tumour (LT) antigen which is capable of immortalising cells only at its permissive temperature (C. A. Petit, M. Gardes & J. Feunteun, Virology 127, 74–82, 1983, P. S. Cat & P. A. Sharp, Mol. Cell. Biol. 9, 1672–1681, 1989). This allows transfected primary tissue cells to be grown indefinitely in culture at the permissive temperature but if cells are required for experimentation then they can be cultured at the restrictive temperature and one would hope that they express genes in the manner of their primary tissue of origin. This does not overcome the problem of multiple and heterologous integration sites of one's transformation constructs.

Cell Lines from Transgenic Animals:

Construction of a transgenic animal results in an organism that has an engineered construct present in all cells in the same genomic integration site. Thus cell lines derived from a transgenic animal will be consistent in as much as the engineered construct will be in the same genomic integration site in all cells and hence will suffer the same position effect variation. This is a small improvement over primary cell immortalisation.

(i) Tumour Derived Cell Lines:

The first and simplest approach has been to transfect cultured murine embryonic stem cells with an immortalising gene construct under the control of a cell type specific promoter. Transformed ES cells can then be injected into a blastocyst from a host mother and the host embryo reimplanted into the mother. One hopes to get a chimeric mouse whose tissues are composed of cells derived from types of embryonic stem cell present in the embryo. Usually the mice from which the ES cells for transformation are derived are chosen to have a different coat colour from the host mouse into whose embryos the transformed cells are to be integrated. Chimeric mice will then have a variegated coat colour. Such mice are then crossed with an appropriate strain in the hope that the germline will also be chimeric and that offspring mice will carry the transgene. It is then hoped that the transgenic mice will develop tumours in the tissues in which the promoter is activated. These tumours can then be cultured as cell lines.

It has been shown that mice transfected with a construct of the SV40 LT antigen under the control of the metallothionein promoter developed tumours of the choroid plexus, and that cell lines can be isolated from these transformed tissues (R. L. Brinster et al, Cell 37, 367–379, 1984). Similarly, it has been shown that in mice transfected with an LT-antigen construct under the control of the 5' regulatory sequences of the insulin gene, tumours developed in the beta-islets of the pancreas (D. Hanahan, Nature 315, 115–122, 1985). This is a clear example of immortalising gene being targeted to the tissue of interest.

Despite these and other successes with this approach it is not ideal. Tumour formation is associated with multiple genetic abnormalities and chromosomal rearrangements (B. Vogelstein et al, N. Engl. J. Med. 319, 525–532, 1988). More often than not the resultant cells no longer express the relevant terminally differentiated genes, or at least not appropriately.

(ii) Conditional Immortalisation of Cell Tissues

A second approach is to transform one's ES cells with a conditional immortalising gene coupled to a broad specificity promoter so that ostensibly the construct is expressed in all tissues in the mouse. If a temperature sensitive immortalising gene is used then the construct will be inactive at the body temperature of the mouse but cells extracted from the mouse can be cultured at the permissive temperature and the cells will be effectively immortalised. It is then hoped that reverting the cultured cells back to the restrictive temperature will restore differentiation specific gene expression and cell cycle arrest, etc. characteristic of the source tissue. This system should produce more reproducible results on cell lines from the same tissues.

(iii) Double-conditionality on immortalisation:

For greater control than approach (ii) one can transform one's embryonic stem cells with a construct carrying the conditional immortalisation gene and a conditional promoter. In this way the immortalisation gene is not really expressed in the cells of the organism but cells in culture can be immortalised at the permissive temperature, in the presence of the factor necessary to activate the conditional promoter. This is a variation on approach (ii) but allows the immortalisation to be under tighter control. One example of such a construct carries the SV40 LT tsA58 antigen under the control of the H02K$^b$ Class 1 promoter. This can be used to transform mice to generate the H-2K$^b$tsA58 mouse (A. Kimura et al, Cell 44, 261–272, 1986), which has been used to generate a number of conditionally immortal cell lines. The H-2K$^b$ Class 1 promoter means that the immortalising construct is only expressed at the permissive temperature of the tsA58 protein and is enhanced by exposure of the cells to interferons (B. David-Wattine et al, Immunol. Today 11, 286–292, 1990) Skin fibroblasts prepared from transgenic mice transformed with this construct yielded proliferating cell lines that could be continuously passaged under permissive conditions. The response of these cell lines to interferons varied, presumably as a result of position effects of the integration site of the construct. Other tissues have been isolated from this system as cell lines, and include enteric glia, bone marrow stroma, osteoclast precursors and primitive kidney cells.

According to a first aspect of the present invention there is provided a cell line derived from a transgenic mammal comprising:
(i) a conditional oncogene, transforming gene or immortalising gene or a cell cycle affecting gene; and
(ii) a cell type specific promoter.

Preferably the cell type specific promoter is derived from a secretory tissue.

Preferred cell lines are a neuronal cell line, a mammary cell line, a liver cell line and a kidney cell line.

Preferred cell type specific promoters are the NF-L gene promoter and the MMTV promoter.

Preferably the conditional oncogene, transforming gene, immortalising gene or cell cycle affecting gene is a SV40tsA58 gene, C Erb β 2 gene or TGFα gene.

The cell cycle affecting gene may however by any gene involved in hyperplasia (excessive formation of cells), cell proliferation or the like.

By utilising a conditional oncogene, transforming gene or immortalisation gene or a cell cycle affecting gene in combination with a cell type specific promoter immortalisation will to some extent be dependant on the differentiation state of the cell. Therefore loss of differentiation specific expression will result in cell-cycle arrest.

A transformation construct of this kind, in which a conditional oncogene, immortalising gene or transforming gene or a cell cycle affecting gene is coupled to a cell type specific promoter, such as the NF-L gene promoter or the MMTV promoter, can be used to generate an immortalised cell line. The conditional oncogene, transforming gene or immortalising gene or a cell cycle affecting gene such as the SV40 tsA58 gene is coupled to a cell specific promoter.

The invention also covers transgenic mammals., particularly rats into whose genomes is integrated at least one recombinant gene whose gene product is involved in oncogenesis, hyperplasia or cell proliferation which may not necessarily be a conditional oncogene like the SV40 tsA58 construct. The invention also applies to transgenic mammals, particularly rats and their progeny who develop hyperplasias or tumours.

The invention also covers the generation of transgenic mammals, particularly rats harbouring tissue specific promoters which drive the expression of cancer causing genes and cell cycle affecting genes, such as ts SV40 T-antigen, c-Erb-B2 and TGF-alpha. The invention also covers cell lines derived from such transgenic mammals, particularly rats.

Transgenic animals are genetically modified animals which harbour at least one experimentally introduced gene. The claimed invention and techniques described are of particular use in generating transgenic animals which can be used as in vivo model systems of normal and diseased tissues, and from which in vitro model systems can be derived. Such model systems are suitable for the study and manipulation of cellular processes in a systematic manner which cannot be achieved with other test systems. Hence they are of great value in elucidating the functions of normal tissue and tissue processes. More importantly they are of value in the validation of candidate drugs and existing drugs, particularly where the model is of a diseased tissue, such as the c-Erb-B2. They are thus of benefit in generating novel therapeutics.

The capability to generate models and cell lines is significant, in that as one moves through the drug development process one can compare the results of in vitro experiments with in vivo experiments more directly.

Toxicological uses of cell lines is also important. Most toxicology is done on whole animals since cell line models of most tissues are unavailable. The conditional immortalisation technique should be amenable to use in other tissues using the relevant tissue specific promoters to generate conditionally immortal cell lines.

The neuronal cell lines developed are of particular significance in that there is no good in vitro model system of normal neuronal tissue in mice, rats or other organisms. Such cell lines will be of benefit for all areas of neuronal research but in particular in drug validation.

Furthermore, having derived an animal from which cell lines can be generated conditionally, one can derive further cell lines by crossing the transgenic animal with animals bearing mutations in other neurone-relevant genes. This will allow researchers to elucidate the roles of such genes and to develop specific in vivo and in vitro disease models.

The benefit derived from the use of the NF-L gene in the transforming construct to generate the neuronal cell lines was unexpected. It is expressed detectably only in post-mitotic neurons so it was surprising that it drove expression of the T-antigen from the SV-40 part of the construct in neuronal precursors. The approach using this construct should be applicable to mammalian systems in general, particularly for the generation of human neuronal cell-lines, particular as a model system in the area of neurodegenerative disease research.

Since mammary tissues are highly secretory-and can be used to secrete protein products, considerable benefit can be derived from developing transgenic animals. A cell line that can be immortalised conditionally is of exceptional value for the generation of transgenic animals or cell lines that secrete particular products either through crossing with other transgenic animals or through direct transgenesis of the animal or derived cell lines.

The approach using for example a MMTV promoter construct should be applicable to mammalian systems in general.

Since current methods for isolating cell lines directly through immortalisation of growing primary cell cultures are inadequate, the applicant has utilised immortalisation of such cells in vivo in transgenic rats Expression of immortalising genes or oncogenes in vivo normally produces tumours and leads to premature death of the animals. However, to allow the mammal, in this case a rat to develop normally the applicant has used an immortalising gene Simian Virus 40 T Antigen gene (or A gene) with a thermolabile mutation of valine for alanine at position 438 (tsA58) (J. Virol 8, 516–524, 1971). The mutated gene is active in the immortalisation process at 33° C. but is inactive at 39° C. due to the thermal instability of its protein product (Proc. Natl. Acad. Sci. USA. 85, 9076–9080, 1988, Proc. Natl. Acad. Sci. USA. 88, 5096–5100, 1991, J. Cell Sci. 108, 37–49, 1993). Rats are chosen since they are a better model for human systems than the other commonly used laboratory animals (eg. mice), and rats are the animals most widely used in the pharmaceutical industry for drug-screening programmes. This was originally because rats are much larger animals than mice and hence they are far more amenable to the surgical manipulations that many pharmacological studies required. The body temperature of the rat is sufficiently high not to permit this mutated Large T Antigen to be functionally active and to immortalise the cells in vivo (Nature 256, 43–46, 1975).

According to a further aspect of the present invention there is provided a method for producing a transgenic mammal, comprising:

(i) causing a female mammal to super-ovulate;
(ii) mating or artificially inseminating the female mammal;
(iii) obtaining the resulting embryo from the female mammal; and
(iv) incorporating
 (i) a conditional oncogene, transforming gene or immortalising gene or a cell affecting gene; and
 (ii) a cell specific promoter into the genome of the mammalian embryo.

Preferably the transgenic mammal is a rat and the female rat is made to super-ovulate by supplying her with a regular supply of Follicle Stimulating Hormone (FSH) prior to mating.

By regular is meant more than a twice daily dose, more preferably more than four daily doses, and more preferably still, continuously.

Preferably the female rat is caused to super-ovulate at approximately 30 days of age by continuous infusion with an effective amount of FSH, preferably purified porcine pituitary FSH.

Preferably a female rat is supplied with 2 mg to 8 mg of FSH, more preferably still about 4 mg of FSH, given over approximately one to four, more preferably still, about two days, immediately prior to mating.

The about 4 mg of FSH is preferably given in a saline solution containing from 10 to 30 mg/ml of FSH, more preferably still about 20 mg/ml FSH.

Preferably the FSH used has a low leutinising hormone (LH) to FSH ratio (about 0.10–0.15) such as that produced by Vetrepharm Inc.

The FSH may be injected by any suitable route. Preferably the FSH is injected intraperitoneally.

Preferably the FSH is delivered by a minipump.

According to yet a further aspect of the present invention there is provided a transgenic mammal whose germ cells and somatic cells contain (i) a conditional oncogene, transforming gene or immortalizing gene or a cell cycle affecting gene; and
(ii) a cell type specific promoter as a result of chromosomal incorporation into the mammalian genome or into the genome of an ancestor of said mammal.

Another aspect of the present invention provides a method for producing a transgenic rat wherein a rat embryo is rinsed substantially free of cumulus cells prior to incorporating an activated oncogene, transforming or immortalizing gene sequence into the genome of the rat embryo.

According to yet a further aspect of the present invention there is provided a method of testing a material suspected of being a carcinogen, said method comprising exposing a mammal produced according to a method of the invention or an ancestor thereof or cells or tissue from a cell line of the invention, to said material and detecting neoplasms as an indication of carcinogenicity.

According to yet a further aspect of the present invention there is provided a method of testing a material suspected of conferring protection against the development of neoplasms, said method comprising treating a mammal produced according to a method of the invention or an ancestor thereof or cells or tissues from a cell line of the invention with said material and detecting a reduced incidence of development of neoplasms, compared to an untreated mammal, as an indication of said protection.

According to yet a further aspect of the present invention there is provided a method of providing a cell line comprising culturing a somatic cell obtained from a transgenic mammal or an ancestor thereof according to the invention.

According to yet a further aspect of the present invention there is provided a cell derived from a cell line obtained from a transgenic mammal or an ancestor thereof according to the invention.

The cells and/or cell lines are preferably tissue specific cell lines, such as, for example, a neuronal In cell line eg NF2C, a mammary cell line eg. B2LT1, a liver cell line, or a kidney cell line. Cell lines NF2C and B2LT1 have been deposited with the ECACC European Collection of Cell Cultures, CAMR (Center for Applied Microbiology and Research), Salisbury, Wiltshire, SP4 OJG, England, as Accession numbers 96092754 and 97032720 respectively.

According to yet a further aspect of the-present invention there is provided a method of providing a transgenic tissue comprising culturing a somatic cell obtained from a transgenic mammal or an ancestor thereof according to the invention.

According to yet a further aspect of the present invention there is provided a tissue derived from a somatic cell obtained from a transgenic mammal or an ancestor thereof according to the invention.

Such a tissue would be of benefit for experimental transplantation and other in vitro work.

Preferably the transgenic rat harbours a tissue specific promoter which drives or controls expression of a cancer causing gene or a cell cycle affecting gene such as tsA58, c-erb B-2 or TGFα. The presence of the promoter may predispose the transgenic rat to cancer, such as breast cancer or to a cell proliferation disorder, for example by over expression of the gene.

Expression of the immortalising gene in the tissue of interest within the transgenic rat is controlled by coupling a tissue-specific promoter that drives the transcription of the immortalising T antigen only within that particular tissue. For example, for targeting expression to the mammary gland the applicant has used the mouse mammary tumour virus (MMTV) promoter (Proc. Natl. Acad. Sci. USA, 82, 5880–5884, 1995) and for targeting expression to neuronal cells the neurofilament light chain (NF-L) promoter (J. Physiol. 84, 50–52, 1990). The former promoter requires activation by hormones released during pregnancy, the latter does not. This targeting technique overcomes the problem encountered previously in transgenic mice which express the tsA58 mutant under the control of a widely-acting constitutive promoter. In that case the mice developed large numbers of tumours in diverse tissues and died at an early age due to revertant mutations in the tsA58 gene (Proc. Natl. Acad. Sci USA 88, 5096–5100, 1991, J. Cell Sci. 104, 37–49, 1993). In the present case cells in the tissue of interest should now grow normally at the restrictive temperature, since they express only the inactive immortalising transgene. However, upon culturing the cells from the tissue of interest at the permissive temperature the immortalising function is activated, and such cells should become immortalised and grow at the permissive temperature (33° C.). They should, however, fail to grow and should differentiate successfully at the nonpermissive temperature (39° C.).

Production of Transgenic Vectors Carrying the tsA58 Gene

As an example, the thermolabile tsA58 gene was coupled to the mouse MMTV promoter which allows expression in pregnant mammary glands (Proc. Natl. Acad. Sci. USA 82, 5880–5884, 1985) and the rat NF-L promoter which allows expression in CNS neuronal cells of the brain (J. Physiol. 84, 50–52, 1990). Both constructs were introduced into a suitable vector using standard techniques (Molecular Cloning—A Laboratory Manual (2nd edition): Cold Spring Harbour Press, New York, 1989). For example the MMTV promoter was introduced into pUC18 (Gene 3, 103–119, 1985) and the NF-L promoter into pPOLYIII (Gene 57, 193–201,1987). It is not clear whether the whole of the A gene region which codes for both Large T and Small t Antigens is required for immortalisation or just the Large T Antigen region is required. Thus as an example, the tsA58U19 variant of the tsA58 gene was coupled to the MMTV promoter. This combination allows the expression of both Large T and Small t Antigens, but it fails to replicate because of a mutation, U19, in the region required for replication of the vector—see FIG. 1A.

FIG. 1A is a plasmid map of the mammary targeting MMTVLTRtsA58U19 construct. A 1.5 kb EcoRI to KpnI fragment of the MMWV LTR containing the start site for transcription, the glucocorticoid response element and the sequences required for mammary specificity, was excised from pMAMneo and ligated into the corresponding restriction endonuclease sites in the cloning vector in pUC18 (Gene 3, 103–119, 1985). Subsequently, the tsA58U19 gene construct containing sequences for both large T antigen and small t antigen, was excised from the BamHI site of pZIPneo (Cell 37, 1053–1062, 1984) and ligated into the BamHI site in pUC18. Restriction endonuclease mapping was carried out to confirm the orientation of the tsA58U19 construct and the identity of the plasmid. The ligation point between the MMTVLTR and tsA58U19 construct was sequenced by the dideoxy chain termination method, to confirm the nature of the ligation point. For the development of transgenic rats, the MMTVLTRtsA58U19 fragment was excised by digestion with EcoRI and SalI, thus minimising the plasmid DNA remaining within the construct.

As the alternative example, the tsA58δt variant of the tsA58 gene was coupled to the NF-L promoter. This combination expresses only Large T Antigen due to a deletion, δt, in the Small t Antigen gene—see FIG. 1B.

FIG. 1B is a plasmid map of the neuronal targeting NF-LtsA58δt construct. A 6 kb HindIII fragment of the human neurofilament light chain promoter (J. Physiol. 84 50–52, 1990) was cloned into the HindIII restriction endonuclease site within the polylinker of the cloning vector pPOLYIII (Gene 57, 193–201,1987). The 6 kbp fragment contained the start site for transcription and is sufficient to confer neuronal specific expression. Subsequently a 2.76 kbp KpnI to BamHI fragment of the tsA58δt, which contains a deletion preventing the expression of small t antigen, was cloned into the reciprocal sites within pPOLYIII. The identity of the plasmid was confirmed by restriction endonuclease mapping. The correct nature of the ligation point was confirmed by dideoxy chain termination DNA sequencing. For the development of transgenic rats the NF-LtsA58δt fragment was excised by NotI restriction endonuclease digestion, minimising the amount of plasmid DNA within the construct.

The excised gene constructs were fractionated by 0.8% agarose gel electrophoresis and the requisite DNA band excised. The DNA was not exposed to ethidium bromide or UV light directly, but a separate marker lane of DNA was run, and used to identify the region of the non-stained gel containing the required fragment. The DNA fragment was then extracted from the agarose slice using the Geneclean Bio 101 kit (2.1.5) with the final pellet being resuspended in a low salt buffer (0.2M NaCl, 20 mM Tris pH7.4, 1.0 mM EDTA). The resulting DNA was further purified using the ELUTIP-d kit (Schleicher and Schuell). Briefly, the ELUTIP-d ionic exchange column was washed with a high salt buffer (1.0 M NaCl, 20 mM Tris HCl pH7.4, 1.0 mM EDTA) and then primed with a low salt buffer (0.2M NaCl, 20 mM Tris HCl pH7.4, 1.0 mM EDTA). The DNA suspension was then run through the column such that the DNA attached to the matrix. Finally the DNA was eluted with high salt solution (1.0 M NaCl, 20 mM Tris HCl pH7.4, 1.0 mM EDTA). The resulting DNA was then ethanol precipitated (2.1) and resuspended in injection buffer (10 mM Tris HCl, 0.1 mM EDTA, pH7.4) at a concentration of 1.5 µg/ml.

Production of Transgenic Rats

Transgenic Sprague Dawley rats were produced by standard methods of microinjection of DNA into the pronuclei of single-cell rat embryos as for transgenic mice (Manipulating the Mouse Embryo. Cold Spring Harbor Press, New York, 1986), except where indicated below. The stud male was mated with a super-ovulating female and the embryos were collected from the oviduct of the female. The transgene in the vector was microinjected into a single pronucleus of a fertilised embryo, which was then introduced into the oviduct of a pseudo-pregnant foster-mother.

The major difference in the technique over that used in transgenic mice was that the female donor rats were found to require a regular/continuous supply of Follicle Stimulating Hormone (FSH) for successful super-ovulation and this was most suitably delivered by a minipump. Without this regular/continuous supply of FSH the injected rat embryos subsequently failed to develop in their foster-mothers. Thus Sprague-Dawley female rats from Charles Rivers Labs, UK were superovulated at 30 days of age by regular/continuous infusion of purified porcine pituitary follicle-stimulating hormone FSH; equivalent to the National Institute of Health (USA) reference standard (NIR-FSH-P1). (Vetrepharm Inc., London, Ontario)) via Alzet mini-osmotic pumps (Alzet model 2001; Alza Scientific Products, Palo Alto, Calif.) (Biol. Reprod. 39, 511–518, 1988). Each pump was filled with 200 μl of FSH diluted to 20 mg/ml in sterile isotonic saline. Pumps were inserted intraperitoneally into pentobarbital-anaesthetized animals, two days prior to mating to deliver 2 mg continuously per 24 hours. Synchronisation of ovulation was induced 48–52 hours later by an intraperitoneal injection of 100 ng luteinising hormone releasing hormone analogue [des-gly10 (D-ala)-LHRH-ethylamide, Sigma]. After mating the females overnight with males of proven fertility and examining for vaginal plugs, all females were sacrificed by cervical dislocation. The pumps were transferred to a second set of animals, and embryos were collected in Dulbecco's PBS from the oviducts (swollen ampullae) of plugged females.

Another difference was that more skill of microinjection of the pronucleus was required over that of the mouse, because of less optical resolution of the pronucleus of the rat compared with that of the mouse. Thus embryos were rinsed free of cumulus cells in 0.1% hyaluronidase and transferred to modified M2 medium for microinjection or modified M16 medium (280 mOsm) for culture at 38.5° C. in 5% $CO_2$ until pronuclei became distinguishable (Manipulating the Mouse Embryo. Cold Spring Harbor Press, New York, 1986). Pronuclear injections were performed on a Nikon inverted microscope equipped with Narishige micromanipulators and Normarski optics. The DNA was dissolved in 1× injection buffer (10 mM Tris HCl, 0.1 mM EDTA, pH7.4) and injected at a concentration of approximately 2 ng/μl (Proc. Natl. Acad Sci. USA, 82, 4438–4442, 1985). After injection of one pronucleus in each embryo (as evidenced by pronuclear expansion), all embryos were transferred to modified M16 medium for incubation until oviduct transfers could be performed.

Transfers of injected embryos into pseudopregnant foster mothers were performed under a standard dissection microscope with a Nikon cold light source. After a solution of 0.1% epinephrine was applied to the ovarian bursa to inhibit bleeding, the bursa was torn to allow access, and the embryos were transferred to the two horns of the oviduct using a finely drawn glass pipette. From experience only bilateral transfers were performed. In addition, embryos were transferred at the pronuclear stage into Day 1-pseudopregnant recipients (synchronous) or, after overnight culture, at the early 2-cell stage into Day 1 (asynchronous) or Day 2 (synchronous) recipients.

These techniques ensured for the first time that transgenic rats could be developed routinely. Further examples of the use of these techniques that the applicants have employed are the introduction of different oncogenes into the pronucleus of the rat embryo and their successful incorporation and expression in transgenic offspring are given later. In all cases after successful births and rearing of the animals, they were mated together to produce the F1 generation.

Animals Bearing the Mammary-targeting Construct

The MMTVLTRtsA58U19 construct contains a 1.5 kbp fragment of the MMTV Long Terminal Repeat (LTR), which contains the elements for glucocorticoid-specific induction, specificity for expression and the start site for transcription, and this was cloned upstream of tsA58U19 (FIG. 1A). After the vector containing this construct was microinjected into embryos, and they were reimplanted and reared in foster-mothers, one founder that contained the transgene was identified out of 43 rats tested. The rats were tested by hybridising the 5' region of the tsA58 gene to DNA isolated from their tails. This represents a success rate of 2.3%. The copy number of transgenes in the founder was two. The F1 progeny produced from the founder rat demonstrated Mendelian inheritance and both hemizygotes and homozygotes have been identified—see Table 1 below.

TABLE 1

Development and Breeding of the Mammary Targeted MMTVLTRtsA58U19 Line of Transgenic Rats

| Generation | Number of animals born | Number of[a] animals containing transgene | Percentage inheritance of transgene | Observed[b] copy number of transgene | Comment |
|---|---|---|---|---|---|
| Founders | 43 | 1 | 2.3% | 2 | Relatively low success rate |
| F1 | 12 | 5 | 42% | 2 | Medelian inheritance |
| F2 | 31 | 22 | 71% | 2 in 16 animals 4 in 8 animals | 8 animals homozygous for transgene |

[a]Determined by Southern hybridisation (in Molecular cloning - A laboratory manual 2nd edition Cold Spring Harbour Press, New York 1989) of 10 μg BamH1 fragmented DNA isolated from tail clips (Manipulating the mouse embryo, Cold Spring Harbour Press, New York, 1986) to a [$^{32}$p] radioactively labelled 2.65 kbp BamH1 fragment of tsA58U19 as a probe (FIG. 1A) followed by autoradiography.
[b]Determined by densitometry of the above autoradiographs and comparison with those of Southern hybridisations containing copy number controls of 1 copy, 10 copies and 100 copies of the transgene per 10 μg of tail DNA. The 2.65 kbp BamH1 fragment of the tsA58U19 gene was used as the transgene for the copy number controls.

The animals suffered no apparent side effects due to the transgene.

Expression of the transgene has been detected by immunocytochemistry using an antibody to Large T Antigen (J. Virol. 39, 861–869, 1981) but only in growing and lactating mammary glands—see FIGS. 2A and 2B and hardarian gland, but in no other organs from lactating rats—see Table 2 below:

FIG. 2A and 2B are immunocytochemical stainings for large T Antigen in the mammary glands of transgenic rats. Mammary glands from mammary-targeted MMTVLRtsA58U19 transgeneic rats incubated with anti-Large T Antigen (Table 2) showing staining in (FIG. 2A) growing mammary glands and (FIG. 2B) lactating mammary glands, 6 days post partum. Magnification×220; Bar= 50 μm.

TABLE 2

Summary of Immocytochemical Detection of Large T Antigen in Transgenic Rats

| Tissue[a] | Staining for Large T Antigen[b] | |
| --- | --- | --- |
| | Mammary-targeted | Neuronal-targeted |
| Mammary gland | +[c] | − |
| Liver | − | − |
| Kidney | − | − |
| Skin | − | − |
| Muscle | − | − |
| Pancreas | − | − |
| Thymus | − | − |
| Spleen | − | − |
| Caecum | − | − |
| Brain | − | +[e] |
| Uterus | − | − |
| Ovary | − | − |
| Cervix | − | − |
| Vagina | − | − |
| Urinary system | − | − |
| Salivary gland | + | − |
| Stomach | − | − |
| Duodenum | − | − |
| Cartilage | − | − |
| Bone | − | − |
| Eye | +[c,d] | − |
| Lung | − | − |

[a]Tissues taken from homozygous 50 day transgenic rats or 1 week lactating transgenic rats (mammary-targeted) or from 50 day homozygous transgenic rats (neuronal targeted), and fixed in Methacarn (J. Histochem Cytochem 37, 1807-1100-1989).
[b]Tissues were immunocytochemically stained with mouse monoclonal antibody pAB 423 to the C-terminus of Large T Antigen (J. Virol 39, 861–869, 1981) and vizualised with the ABC method (Cytochem 29, 577–601. 1981), as described previously (Cytochem 41, 877–893, 1993).
[c]Lactating glands, epithelial cells only.
[d]Hardarian gland only.
[e]Fibres of the internal capsule and choroid plexus.

Animals Bearing the Brain-targeting Construct

The NF-LtsA58δt construct contains a 6 kbp fragment of the human neurofilament light chain promoter, which, itself contains the elements required for specific expression and also the start site for transcription, and this was cloned upstream of tsA58dt. After the embryos were microinjected with this vector and reared in foster-mothers, one founder was identified from 15 rats screened, a success rate of 6.7%. The founder was shown to be mosaic, as the resultant progeny did not inherit the transgene in a Mendelian manner—see Table 3 below.

TABLE 3

Development and Breeding of the Neuronal Targeted NF-LtsA58δt Line of Transgenic Rats

| Generation | Number of animals born | Number of[a] animals containing transgene | Percentage inheritance of transgene | Observed[b] copy number of transgene | Comment[c] |
| --- | --- | --- | --- | --- | --- |
| Founders | 15 | 1 | 6.7% | 2 | Anticipated success rate |
| F1 | 24 | 3 | 12.5% | 6 | Mosaic inheritance |
| F2 | 34 | 19 | 56% | 6 | Subsequent Medelian inheritance |

[a]Determined as for Table 1
[b]Determined as for Table 1
[c]The NF-LtsA58δt transgene was inherited in a non-Mendelian mosaic manner on breeding of the founder rat, i.e. it was not incorporated into the genome of the embryo until the embryo had reached at least the two cell stage. The observed copy number of the transgene was also lower in the founder animal than in subsequent generations due to the transgene not being present in all cells. Subsequent breeding exhibited Mendelian inheritance. Hemizygous animals have been identified and have been crossed, although their progeny are awaiting analysis.

The copy number of the transgene in the F1 was approximately 6. At present only hemizygous animals have been identified. Subsequent breeding of the hemizygous animals has exhibited Medelian inheritance (Table 3).

Expression of the transgene has been identified by immunocytochemistry, using antibody to Large T Antigen, in various regions of the adult brain, but in no other organs (Table 2). The most intense staining was found in the fibres of the internal capsule which are the major neuronal highway between the thalamus and the cortex—see FIG. 2C. Staining was also noticed in the choroid plexus which is involved in the production of cerebro-spinal fluid—see FIG. 2D.

FIGS. 2C and 2D illustrate immunocytochemical staining for Large T Antigen in the brains of transgenic rats. Brain from neuronal-targeted NF-LtsA58δt transgenic rats incubated with anti-Large T Antigen above showing staining in (FIG. 2C) fibres of the internal capsule and (FIG. 2D) choroid plexus. Magnification×220: Bar=50 μm.

The NF-LtsA58δt transgenic rats suffer side effects potentially due to the transgene in later life. Three animals developed choroid plexus tumours which showed high levels of staining for Large T Antigen. The development of tumours may be due to the reversion of the transgene to that of the wild-type. A number of animals have also died due to renal failure, but the expression of the transgene could not be detected in this organ.

Production of Cell Lines from Mammary-targeted Tissue

Primary cultures were established from the mammary glands of 50-day old virgin female rats that express the mammary-targeted T Antigens by digestion with collagenase (J. Cell Biol. 73, 561–577, 1977). Fibroblasts were removed by preplating or by centrifugation through percoll gradients (In Vitro 22, 429–439, 1986). The primary cultures were grown in 50% DMEM, 50% RPMI, 10% FCS, 20 ng/ml EGF, 50 ng/ml hydrocortisone, 50 ng/ml insulin and medium exposed to UV-irradiated Rama 27 feeder fibroblasts (In Vitro, 25, 23–36, 1989). The primary cultures were transferred by treatment with EDTA (Cell 15, 283–298, 1978). After 4 passages, an epithelial-like cell strain was established—see FIG. 3A.

FIGS. 3A and 3B are a B2LT1 cell line from the mammary glands of mammary-targeted MMTVLTRtsA58U19 transgenic rats.

Figure 1A:
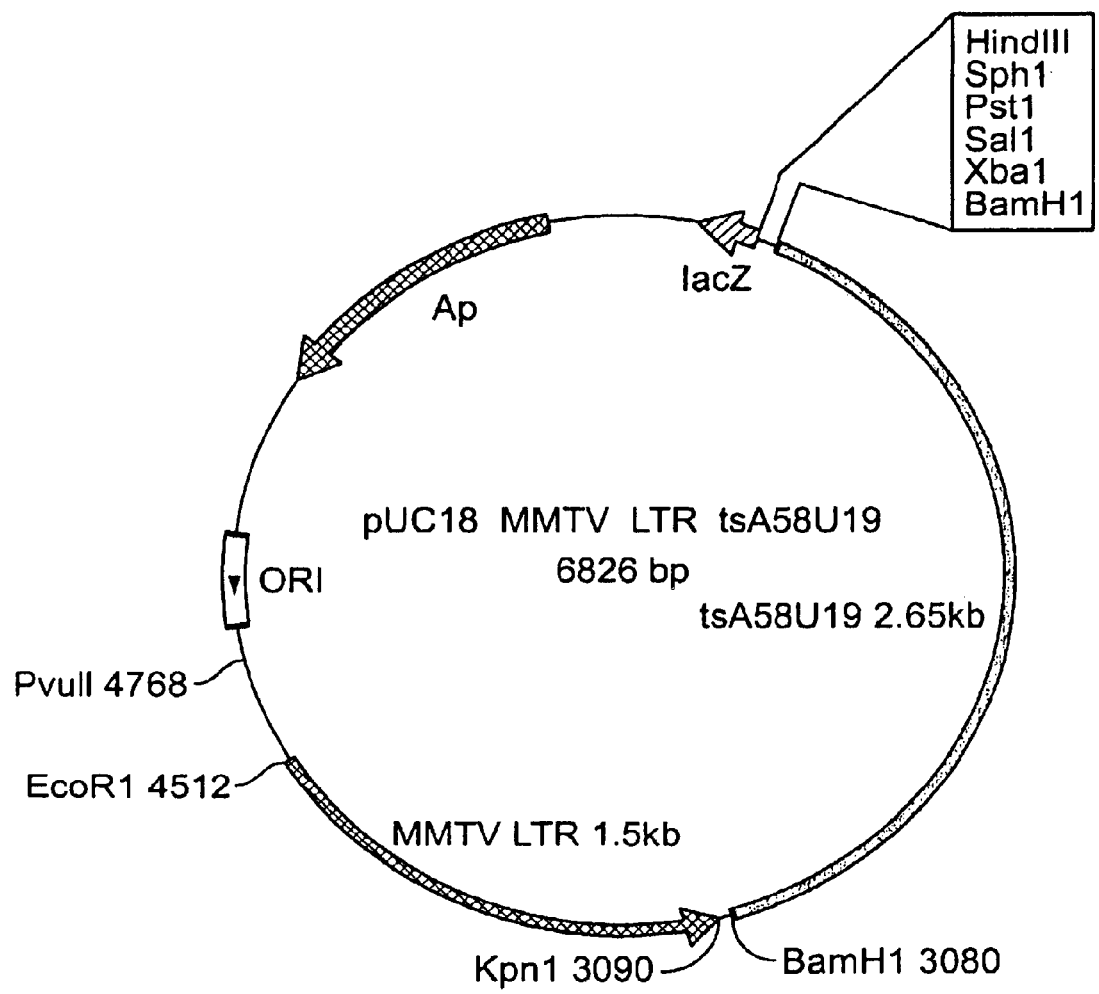
Figure 1B:
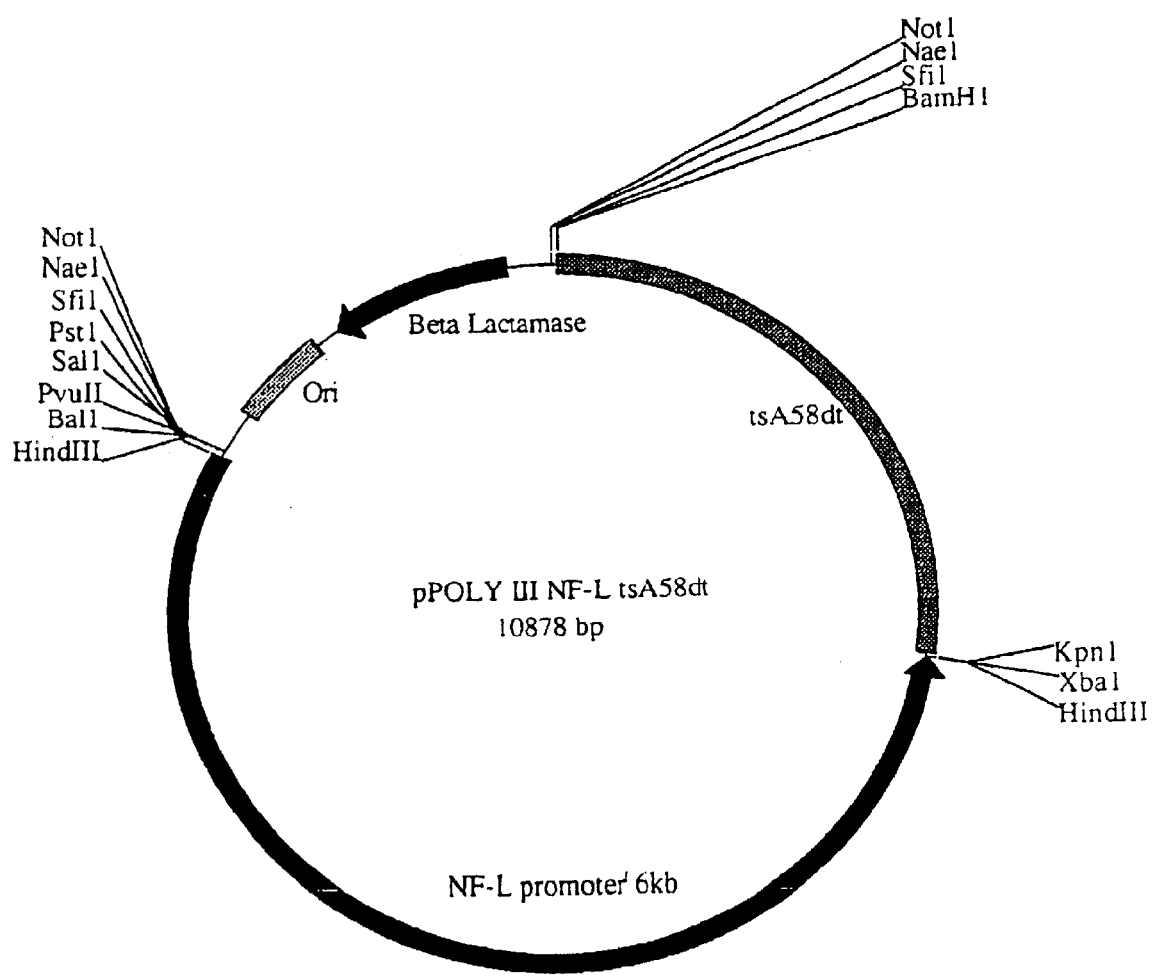
Figure 2B:
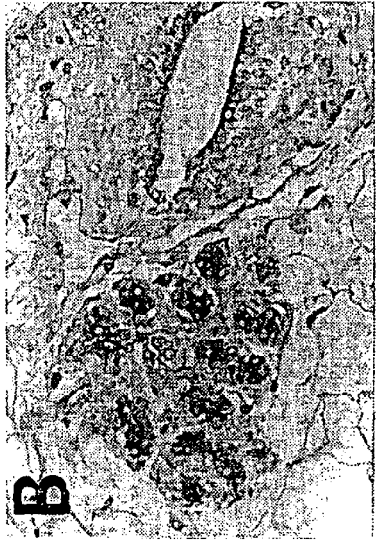
Figure 2D:
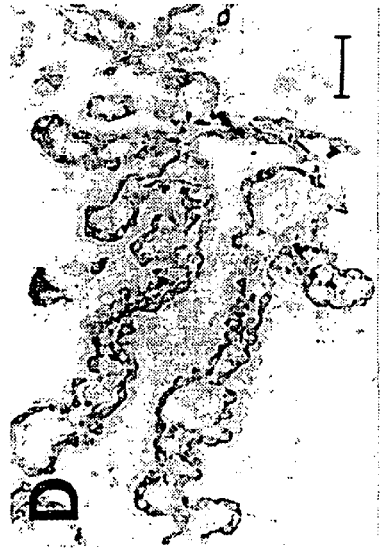
Figure 2A:
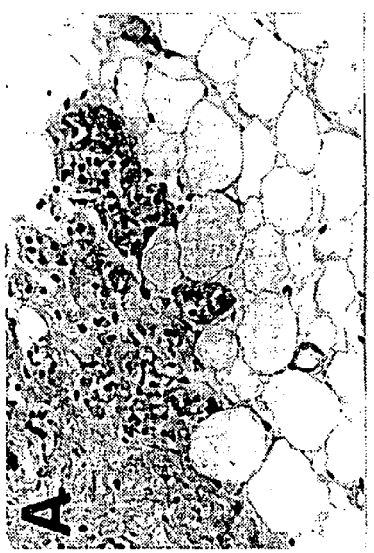
Figure 2C:
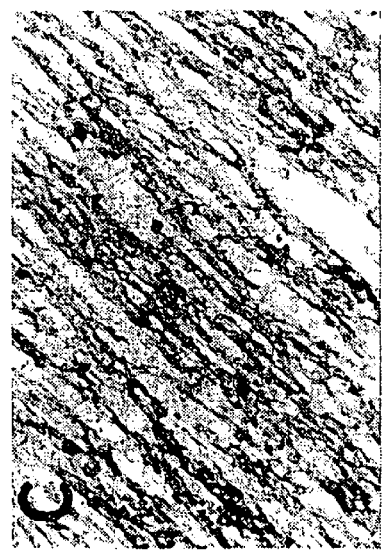
Figure 3B:
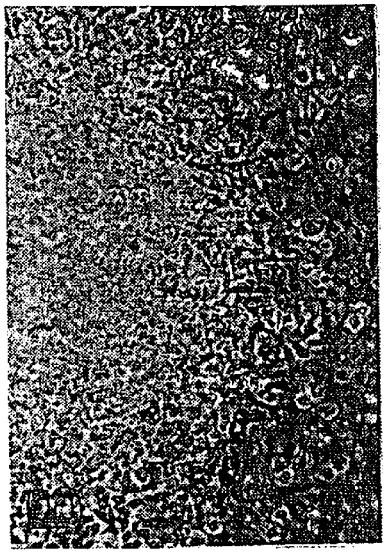
FIGS. 3A–3D show phase-contrast macrographs of all cell lines produced from transgenic rats at a magnification of X200, Bar=50 μm.
Figure 3D:
Figure 3A:

In FIG. 3A the cell line was kept at 33° C. and shows an epithelial-like intermediate morphology, and in FIG. 3B the cell line was kept at 39° C. with 5 ng/ml prolactin and shows a dark droplet cuboidal morphology with associated hemispherical blisters or domes reminiscent of cultured alveolar cells.

Figure 3C:
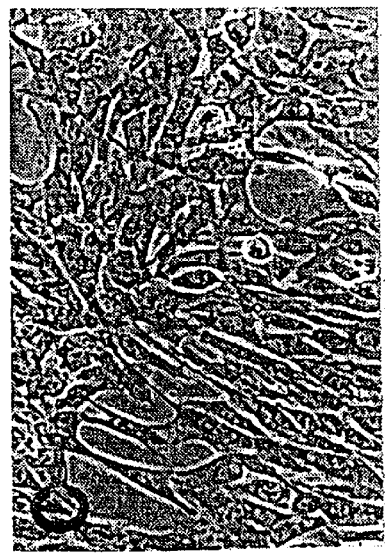

FIGS. 3C and 3D are a NF2C cell line from the brain of neuronal-targeted NF-LtsA58δt transgenic rats.

In FIG. 3C the cell line was kept at 33° C. and shows more-elongated cells, and in FIG. 3D the cell line was kept at 39° C. with 5 ng/ml basic fibroblast growth factor and shows dendritic-like outgrowths.

This epithelial like cell strain from the mammary glands was cloned and stored in frozen aliquots. The cloned cell line B2LT1 has been characterised by immunofluorescence, and it stains for milk fat globule membrane, cytokeratins and peanut lectin, as well for Large T Antigen (J. Virol 39, 861–869, 1981)—see Table 4 below.

TABLE 4

Immunofluorescent Staining of Mammary-Derived B2LT1 Cells for Mammary Specific Markers and Large T Antigen

| Antibody or reagent[a] | Cell type specific marker | Immunofluorescence[b] | |
|---|---|---|---|
| | | 33° C. | 39° C. |
| Anti-milk fat globule membrane | epithelial | + | ++ |
| Anti-cytokeratin | epithelial | ++ | +++ |
| Peanut lectin | epithelial/alveolar | - | ++ |
| Anti-smooth muscle actin | mycepithelial | + | + |
| Pokeweed mitogen | mycepithelial | ++ | ++ |
| Anti-vimentin | mycepithelial/fibroblast | +++ | ++ |
| Anti-Large T Antigen | immortalised | +++ | + |

[a]Antibodies and reagents used are rabbit anti-rat milk fat globule membrane, rabbit antihuman callus keratin, peanut lectin (E.Y. Labs, San Mateo, California), mouse monoclonal antibody (MAb) MA933 to smooth muscle actin (EnZo Biochemicals, N.Y.) (J. Histochem. Cytochem. 37 1089–1100, 1989), pokeweed mitogen (J. Histochem, Cytochem 38, 1633–1649, 1990), mouse MAb V9 to vimetin (Dako Labs, High Wycombe, Bucks) (J. Histochem. Cytochem 37, 1089–1100, 1989), and mouse MAb to pAB to the N-te
[b]B2LT1 cells containing the tsA58 gene construct were grown at the restrictive temperature of 33° C. and the permissive temperature of 39° C. for several days, and the bound antibodies were vizualised either indirectly using the appropriate second antibody conjugated to FITC or, for the two lectins, directly conjugated to FITC, in a Polyvar microscope with epifluorescent optics using a B1 filter block (In Vitro 25, 23–36, 1989. The percentages of fluorescent cells were recorded as follows: +++, 50–75%; ++, 25–50%; +, 5–25%; and –, <5%.

It therefore exhibits some properties of epithelial cells (J. Histochem. Cytochem. 37 1087–1100, 1989). However, the epithelial-like cells convert to a more-elongated, anti-vimentin, pokeweed mitogen (J. Histochem Cytochem. 38, 1633–1645; 1990) and weakly anti-actin staining myoepithelial-like phenotype (J. Histochem. Cytochem. 37, 1087–1100, 1989) in culture. This result is consistent with the original epithelial cells being mammary epithelial stem cells (Histol. Histopathol. 8, 385–404, 1993). When they were grown at the restrictive temperature for the transgene in the presence of prolactin, B2LT1 cultures ceased to divide—see FIG. 4A and took on the appearance of alveolar cells in culture (FIG. 3B) (Eur. J. Biochem. 133, 707–715, 1993) and showed enhanced staining for epithelial/alveolar cells and reduced staining for myoepithelial-like cells—see Table 4 above.

Figure 4A:
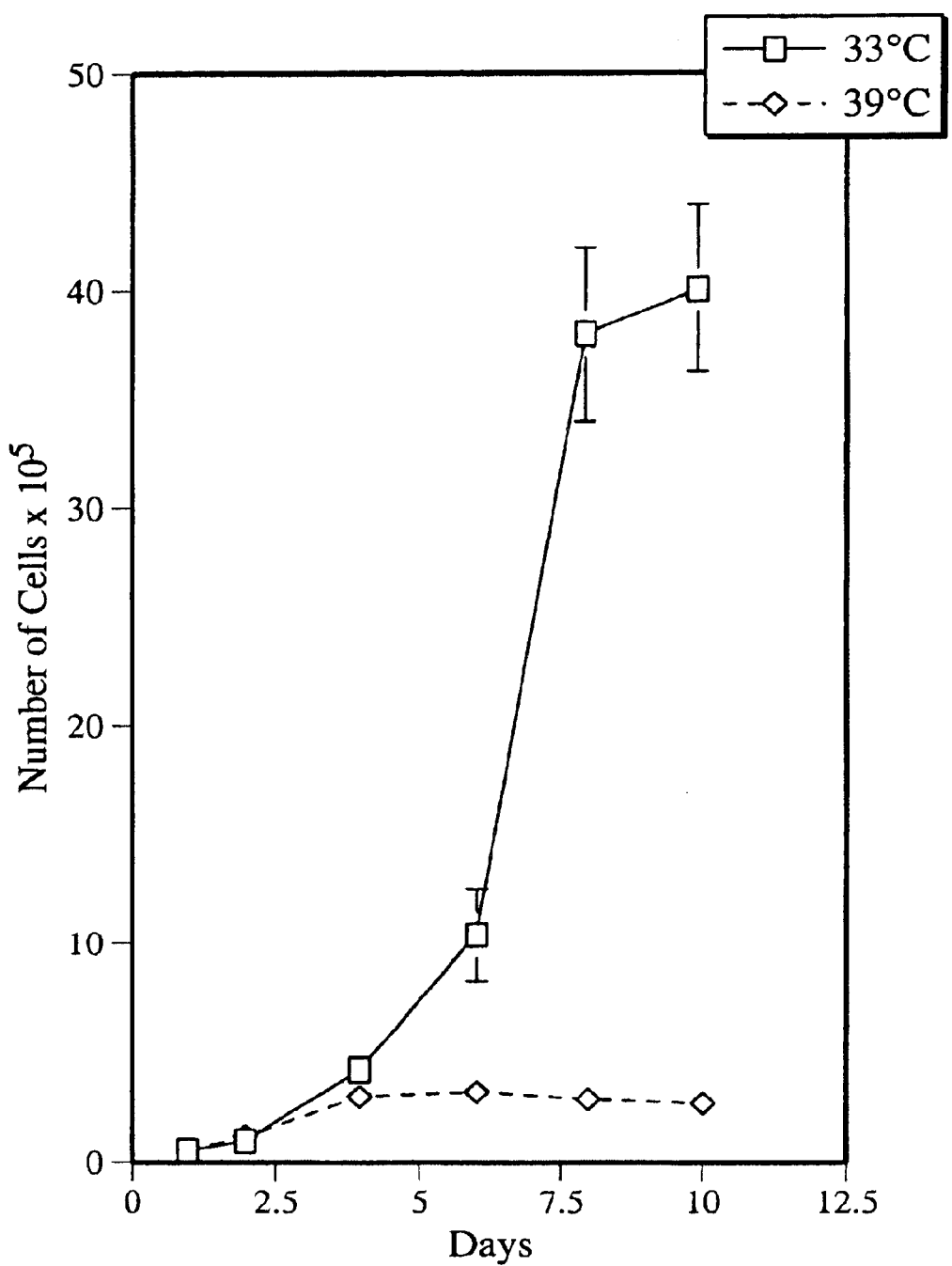

FIG. 4A shows the growth curves for mammary derived B2LT1 cells. The B2LT1 cells were seeded at a density of 6×10⁴ cells per plate and incubated at 33° C. for 24 hours after which time half of the cells were transferred to an incubator at 39° C. Cell numbers were counted for quadruplicate replica plates, at two day intervals using a Coulter counter. The means±SE are shown.

TABLE 5

Immunochemical Staining of Brain-derived NF2C Cells for Neuronal-Specific Markers and Large T Antigen

| Antibody to[a] | Neuronal cell marker type | Immunochemical staining[b] | |
|---|---|---|---|
| | | 33° C. | 39.5° C. |
| Neuron-specific enolase | Neuron | – | +++ |
| Synaptophysin | Neuron | – | ++++ |
| MAP2 | Neuron | ++ | ++++ |
| Tau | Neuron | – | + |
| Neurofilament light chain | Neuron | ++ | ++++ |
| GFAP | Glial cell | ++ | – |
| Large T Antigen | Immortalised | +++ | + |

[a]Antibodies used are: for neuron-specific enolase, polyclonal from Polysciences Inc., Warrington, Cheshire (Ann. Rev. Neurosci. 10, 269–295, 1987); for synoptophysin, MAb MCA 860 from Serotec Ltd., Oxford (Cell 41, 1017–1018, 1985); for microtubule-associated protein 2 (MAP2), MAb M-P1406 from Sigma Immunochemicals, Poole, Dorset (Neurosci 11 29–44, 1988); for tau, MAb T-5530 from Sigma Immunochemicals (J. Cell Biol. 102 252, 262, 1986); for neurofilament light chain (68 kd), MAb N-513 from Sigam Immunochemicals (Proc Natl. Acad. Sci. USA 79, 1326–1330, 1982); for glial fibraillary acidic protein (GFAP), MAb MCA 363 from Serotec Ltd. (J. Cell Biol 88, 115–126, 1982).
[b]NF2C cells containing the tsA58δt gene construct were grown at the restrictive temperature of 33° C. or the permissive temperature of 39° C. and protein was isolated by cellular fractionation on a Cs Cl gradient (Biochemistry 18, 5294–5299, 1979). The proteins (10 μg) were separated on a 12.5% sodium dodecylsulphate polyacrylamide gel, Western blotted (Molecular Cloning - A laboratory Manual (2nd edition); Cold Spring Harbour Press, New York, 1989) with the requisite antibodies which were in turn located using the ABC method (J. Cell Biol. 102, 252–262, 1986; Proc Natl. Acad. Sci. USA 79, 1326–1330, 1982). and finally visualised by chemiluminescence (Clin. Chem 25, 1531–1546, 1989) which was radioautographed (Amersham Life Sciences, Bucks.).

The level of chemiluminescent staining for the neurone-specific markers was assessed by densitometry of the radioautographs and comparison with the level for 10 μg of rat brain extract which was arbitarily set at 100%. The levels of Chemiluminescent staining were recorded as follows: ++++. 75–100%; +++, 50–75%; ++, 25–50%; +, 5–25%; and –, <5% of the level of rat brain extract. The level of chemiluminescent staining of MAb pAB 419 to the N-terminus of Large T Antigen (J. Virol 39, 861–869, 1981) was assessed relative to that of 10 μg of protein of the Huma 62 SV40-immortalised cell line (Dec. Bio. 136, 167–180, 1989) arbitarily set at 100%.

The B2LT1 cells have now lost the requirement for feeder cells in culture and grow rapidly at 33° C. with a doubling time of 22 hr. The cells grow to a density of 4×10⁶ per 9 cm diameter plate and when split at a ratio of 1:10 are confluent after 3 days at 33° C.

Production of Cell Lines From Tissue Containing the Brain-targeted Transgene

Cell lines were developed by establishing primary cultures of brain cells of an adult male by digestion with trypsin and culturing them at 33° C. in 50% DMEM, 50% RPMI, 10% FCS with added pyruvate, glutamine, NaHCO₃ and 50 ng/ml insulin (Dev. Neurosci. 5, 2197–2200, 1994). The cells were transferred as above. At crisis, the more abundant glial and fibroblast cells died out allowing the slower-proliferating neuronal cells to be cultured. These were eventually cloned, one such clone was designated NF2C, and it was cultured and stored in aliquots at −70° C.

Figure 4B:
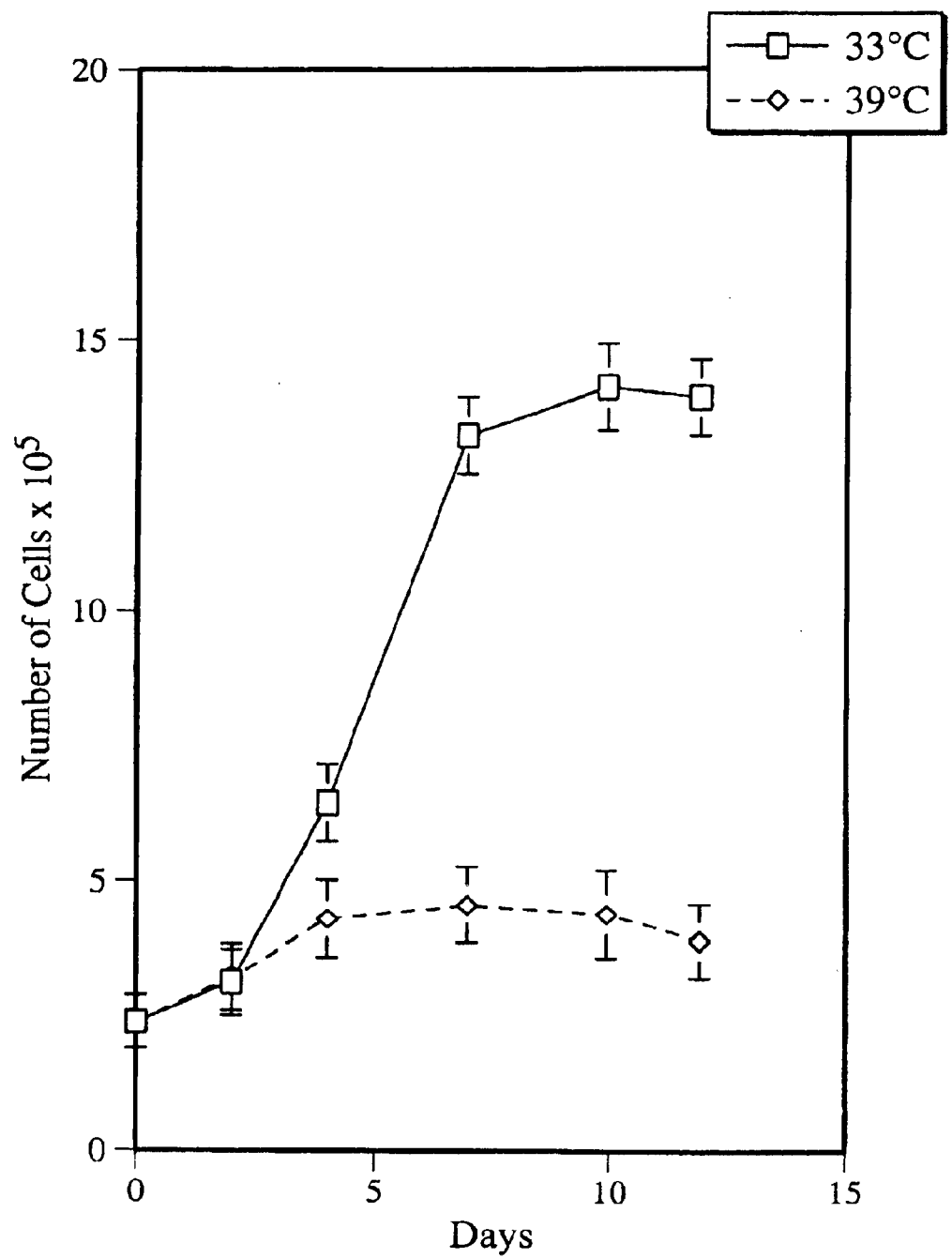

The cells grow successfully at 33° C. in 50% DMEM, 50% RPMI, 10% FCS and 50 ng/ml insulin (In Vitro, 25, 23–36, 1989), with a doubling time of 36 hr and grow to a density of approximately $2\times10^6$ per 9 cm diameter plate. At the restrictive temperature of 39° C. the cells ceased to divide—FIG. 4B FIG. 4B shows the growth curves for brain-derived NF2C Cells. The NF2C cells were seeded at a density of $2\times10^5$ cells per plate and incubated at 33° C. for two days, such that the cells may become established after passaging. After 2 days, half of the plates were transferred to an incubator at 39° C. Cell numbers were counted for quadruplicate plates at three day intervals using a Coulter counter. The means±SE are shown.

At 33° C. the cells are elongated (FIG. 3C) which becomes further exaggerated at 39° C. (FIG. 3D). The cell line has been characterised by Western blotting of cellular extracts with suitable antibodies for neuronal markers—see FIG. 5.

Figure 5:
Figure 5:
Figure 5:
Figure 5:
Figure 5:
Figure 5:

FIG. 5 shows immunochemical detection of neuronal markers in brain derived cells in NF2C. Proteins (10 µg) (A) from homogenised brains of normal rats; (B) from a rat mammary-epithelial cell line Rama 37 (Cancer<etastasos Rev. 6, 55–83, 1987); (C,D) from the brain-derived and neuronal-targeted NF-LtsA58δt cell line NF2C grown at (C) 33° C. or (D) 39° C. with 5 ng/ml basic fibroblast growth factor were electrophoresed on 12.5% sodium dodecylsulphate polyacrylamide gels and subject to Western blotting (Molecular cloning—A Laboratory Manual (2nd Edition): Cold Spring Harbour Press, New York, 1989) with antibodies to markers of neuronal cells: neuron-specific enolase (Ann. Rev.Neurosci. 10, 269–295, 1987), synaptophysin (Cell 41, 1017–1028, 1985), MAP2 (Ann. Rev. Neurosci. 11, 29–44, 1988), tau (J. Cell Biol. 102, 252–262, 1986), neuraofilament protein (Proc. Natl. Acad. Sci. USA., 79, 1326–1330, 1982) and to a marker of glial cells, GFAP (J. Cell Biol. 88, 115–126. 1982). The antibody-bound proteins were visualised by the ABC method (J. Histochem. Cytochem. 29, 577–601, 1981) using chemiluminescence (Clin. Chem. 25, 1531–1546, 1979) as for Table 5. The chemiluminescence was photographed using a MacIntosh computer video capture, and the Image 1.44 VDM-F photo programme. Molecular weight marker proteins were run in parallel and the molecular weights of the stained bands were recorded.

The cells express neuron-specific enolase (Ann. Rev. Neurosci. 10, 269–295, 1987), synaptophysin (Cell 41, 1017–1028, 1985), microtubule-associated protein 2 (MAP2) (Ann. Rev. Neurosci. 11, 29–44, 1988), tau (J. Cell Biol. 102, 252–262, 1986) and neurofilament protein (Proc. Natl, Acad. Sci. USA. 79, 1326–1330, 1982) strongly at 39° C. and more weakly or not at all at 33° C. The glial marker 1 glial fibrillary acidic protein (GFAP) (J. Cell Biol. 88 115–126, 1982) was expressed weakly at 33° C. but not at 39° C., and Large T Antigen was identified at both temperatures (Table 5). Expression of the neuronal-specific markers and dendritic outgrowths was increased if the cells were grown in medium containing basic fibroblast growth factor which acts like a short-acting nerve growth factor for 6–7 days in these systems (J. Neurosci 5, 307–316, 1985). These results suggest that the cell line from the brain is of neuronal origin and that it may possess certain stem cell characteristics being capable of expressing glial markers as well as neuronal markers but only at the permissive temperature.

Examples of the use of this invention are shown below for product production, drug discovery, toxicology, and gene manipulation including gene therapy.

Product Production

Although rarely-occurring genetically engineered proteins can be synthesised in lower organisms such as bacteria and yeast, the modifying enzymes that are required, for example, to glycosylate and phosphorylate proteins correctly are usually absent. This may result in inactive proteins or their rejection by the immune system of higher organisms, including humans. Hence higher eukaryotic systems are required for the synthesis, correct processing and secretion of recombinant proteins for rare products that may be ultimately used in animals and humans. Some differentiated animal tissues specialise in secreting large amounts of correctly processed proteins, one such example is the breast during lactation. Thus the ability to produce recombinant proteins in fully differentiated cell lines from such tissues would be of enormous benefit to the health care and pharmaceutical industry. As an example human insulin, interferons and other hormonal agents and their receptors may be produced by transfecting the requisite constructs with suitable (e.g. mammary-specific) promoters into conditionally immortalised mammary cell lines. These transfected cell lines may be grown on an industrial scale at the permissive temperature and then induced to differentiate at the restrictive temperature into nondividing secretory cells containing all the necessary protein synthetic, processing, modifying and secreting apparatus.

Drug Discovery

The development of differentiating cell lines from organs where no suitable cell lines exist (e.g. neuronal cells from the brain in general or even various regions of the brain such as the substantial nigra for Parkinson's disease) would be of enormous benefit, enabling new receptors for cell signalling molecules to be identified and isolated. These receptors may have novel physiological and pharmacological effects. Moreover, existing and potential agonists and antagonists of known and novel receptors may be screened rapidly in suitable differentiated cell lines. Since these cell lines are of rat origin, results with different agonists and antagonists may be translated more rapidly into pharmacological use in vivo in the experimental animal that is employed normally by the pharmaceutical industry for this purpose.

Transgenic rats containing other oncogenic, transforming or immortalising genes correctly targeted to the tissue of interest can also be produced using this technology for such purposes as the screening of drugs in viva that inhibit oncogenesis. Examples include rats expressing transforming growth factor alpha and c-erb-B2, both of which produce breast lesions similar to those encountered in the human disease, as described later.

Toxicology

Many hundreds of thousands of rats are utilised in the pharmaceutical and other industries for the testing of potential harmful or toxic effects of chemicals that may be inadvertently or advertently exposed to humans, either by digestion, inhalation or by direct contact. Tests for toxic effects on a cultured cell line are comparatively quick, taking only a few days at most, compared with several months for animal tests; they are direct; and they are reproducible, not being subject to the vagaries of metabolic processes of the body. Thus the ability to produce differentiated cell lines of the organs most likely to be afflicted by different substances from the animal routinely employed for such tests in vivo would speed up enormously the testing process and at the same time reduce dramatically the very expensive requirement for such large numbers of rats. At present the most likely organs to be subjected to internal toxic damage are the liver, kidneys and brain, and there are no satisfactory normal cell lines showing true differentiated characteristics from any of these tissues. Such conditionally immortalised cell lines could be derived from transgenic rats carrying the tsA58 gene coupled to known tissue promoters that allow only expression in the required tissue.

Gene Manipulation Including Gene Therapy

The ability to produce well differentiated cell lines means that they can be genetically modified in culture by transfection of new constructs for assistance in the discovery of new drugs. An example is the coupling between a receptor and its correct effector. This coupling can be investigated much more readily through a suitable fluorescent reporter-gene construct, e.g. cAMP-responsive luciferase-reporter gene. Hence screening for potential agonists/antagonists would be accelerated greatly using this approach. A second example is the use of antisense technology which can be utilised only in cultured cells at present to identify which effector/G proteins are coupled to a particular receptor and hence identify the specific effector/coupling molecules for drug targeting. A third example is to identify the molecular mechanism for receptor desensitisation for future intervention therapy in cases of drug-addiction using a physiologically more relevant system than the chinese hamster embryo fibroblasts employed currently. A fourth example would be transfection of disease-associated gene or gene knock-out constructs into suitable target cell lines, to model a disease phenotype either in vitro or by transplantation into syngeneic rats in vivo, e.g. transfection of the Swedish mutation of the amyloid precursor protein into the neuronal cell line for production of a model for Alzheimers disease and its phenotypic reversion using antisense technology.

Generation of Transgenic Rats as Models for Human Cancers

Although transgenic mice expressing transgenes which are thought to be involved in human cancers have been produced (Cancer Metastasis Rev. 10, 217–227, 1991, Cancer Surveys 16, 97–113, 1993, Cancer Invest. 12, 203–213, 1994), none have as yet been expressed in rats to yield a successful model of the equivalent human disease. As an example targeting of expression to the rat mammary gland of two potential oncogenes is shown using the technology outlined earlier in this patent.

In order to create transgenic rat models which mimic human breast cancer, it was decided to target overexpression of the oncogenes transforming growth factor alpha (TGFα) and c-erbB-2 (HER-2) to the mammary glands. TGFα is a mitogenic polypeptide that structurally and functionally resembles Epidermal Growth Factor (EGF) (Proc. Natl. Acad. Sci. USA. 80, 4684–4688, 1983). Minimal expression of inmmunoreactive TGFα is detectable in normal human breast tissue, but increased expression occurs in ductal hyperplasia, atypical hyperplasia and ductal carcinoma in situ (J. Clin. Pathol. 45, 513–516, 1992). Immunoreactive TGFα has also been detected in 30–70% of human breast carcinomas and its presence correlates with tumour burden (Histochem. J. 26, 355–366, 1994, Am, J.Pathol. 138, 1527–1534, 1991, Virchows Archiv. A. Pathol. Anat. 420, 345–351, 1992).

The c-erbB-2 gene product has also been strongly implicated in the development of human breast cancer. This proto-oncogene encodes a tyrosine kinase receptor that is structurally related to the EGF receptor (Science 230, 1132–1139, 1985, Nature 319, 230–234, 1986) and is the human homologue of the transforming rat oncogene neu (Nature 290, 261–264, 1981) which contains a point mutation in the transmembrane domain of the protein that results in constitutive tyrosine kinase activity (Cell 45, 649–657, 1986). The level of c-erbB-2 in normal human breast tissue is very low (Oncogene 5, 953–962, 1990), but in invasive breast carcinomas expression of c-erb-B-2 is observed in 20–30% of breast tumours, which in some cases is accompanied by gene amplification (Ir. J. Med. Sci. 158, 137–140, 1989, Br. J. Cancer 63, 447–450, 1991, Science 235, 177–182, 1987). An inverse correlation has been noted between patient survival and c-erb-B2 expression, particularly in patients with no involved lymph nodes (Br. J. Cancer 63, 447–450, 1991, Science 235, 177–182, 1987).

Production of Transgenic Vectors Carrying the Oncogenes

As an example it was decided to use the mouse mammary tumour virus promoter (MMTV) linked to the Rous Sarcoma Virus (RSV)-LTR enhancer to drive expression of TGFα and nonmutated c-erbB-2 in the mammary glands. Constructs were made by subcloning human cDNAs for TGFα or c-erbB-2 downstream of the MMTVLTR promoter. To provide an intron to enhance expression of the cDNAs and a splice and polyadenylation signal to ensure correct processing of the transcript, a 700 bp fragment from the 3' end of the human growth hormone gene was placed downstream of the cDNAs—see FIG. 6

Figure 6:
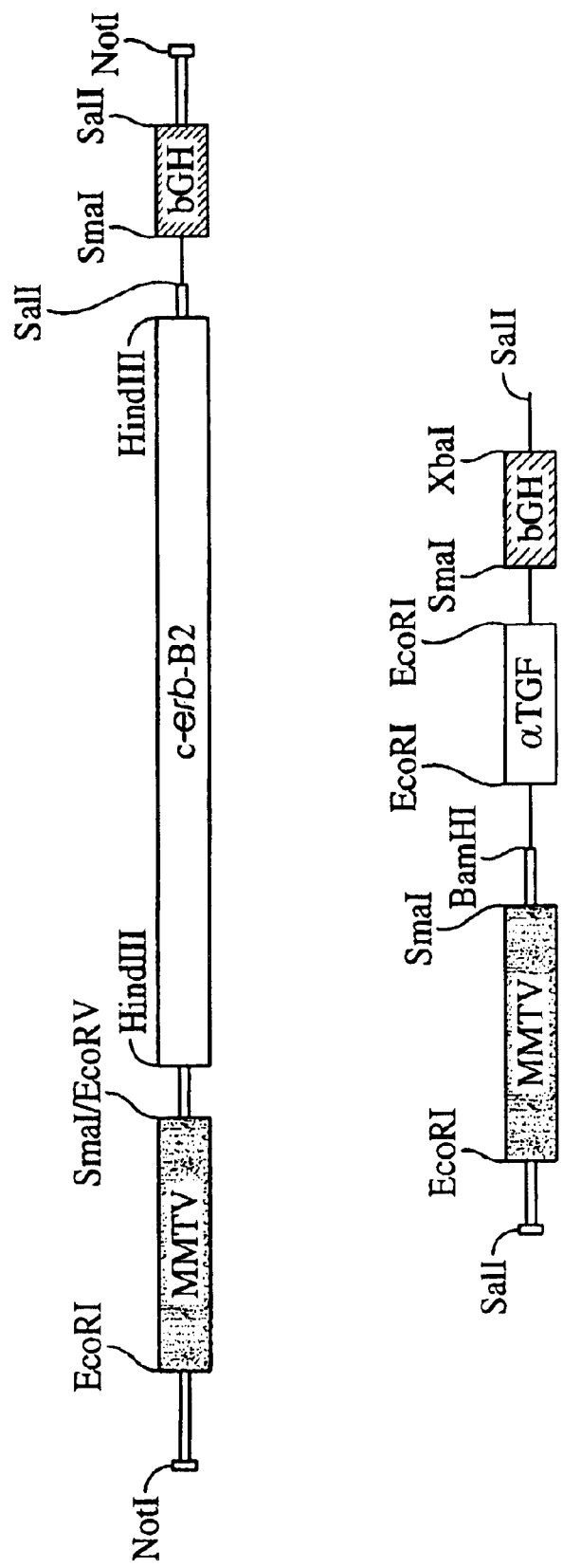

FIG. 6 illustrates the structure of the mammary targeting MMTVLTR-TGFα and MMTVLTR-c-erbB-2 constructs. The diagram shows the structure and important restriction sites utilised in the construction of the transgene. The MMTV-LTR promoter is used to drive expression of the downstream oncogenes, and a 3' fragment of the human growth hormone (hGH) gene ensures correct processing of the transcript. Thick and thin lines represent sequences derived from the polylinkers of plasmids pPolyIII-I and pBluescript, respectively. The completed transgenes were released from their parental plasmids by digestion with restriction enzymes, purified and microinjected into rat embryos.

Production of Transgenic Rats

Transgenic rats were identified by Southern blot analysis of tail genomic DNA, as described previously. The animals contained from less than one up to 50 copies of the integrated transgene per haploid genome, as shown in Table 6 below, with the exception of one of the male MMTVLTR-TGFα founders, all the offspring were fertile and were mated successfully.

TABLE 6

Generation and Breeding of Mammary Targetted MMTVLTR-TGFα and MMTVLTR-c-erb B2 Transgenic Rats

| Founder | Sex | Copies of[a] transgene | Successfully mated | Mosaic or Mendelian inheritance |
|---|---|---|---|---|
| TGF/1 | Female | 5–10 | Yes | Mendelian |
| TGF/2 | Female | 1 | Yes | Mosaic |
| TGF/3 | Male | 10 | Yes | Mosaic |
| TGF/4 | Male | 10 | Yes | Mosaic |
| TGF/5 | Male | 5–10 | Yes | No transmission |
| TGF/6 | Male | 1–5 | No | Unknown |
| ERB/1 | Female | 10–20 | Yes | Mendelian |
| ERB/2 | Female | 1–5 | Yes | Mendelian |
| ERB/3 | Female | ~50 | Yes | Mendelian |
| ERB/4 | Male | 1 and >20 | Yes | Mendelian two integration sites |
| ERB/5 | Female | <1 | Yes | Unknown |
| ERB/6 | Female | 5–10 | Yes | Mosaic |
| ERB/7 | Male | 1 | Yes | Sex linked-transgene on Y chromosome |

[a]Determined as for Table 1 of rats in text using either [$^{32}$P]radioactively labelled EcoRI fragment of the cDNA for αTGF or a HindIII fragment of the cDNA for c-erb B-2 as probes. The same fragments were used as the transgene for copy number controls.

Five of the founders transmitted the transgene in a Mendelian fashion to their offspring and four other founders transmitted the transgene at a much lower frequency; these latter founder animals were probably mosaics. No transmission was observed from one line of MMTVLTR-TGFα transgenics and one of the MMTVLTR-c-erbB-2 female animals appeared to be sub-fertile because only one litter was obtained; all the animals from this single litter were negative for the transgene. It was not possible to analyse any females from another of the MMTVLTR-c-erbB-2 lines (ERB/7) because the transgene appeared to integrate into the Y chromosome; all male offspring inherited the transgene but no female transgenic offspring were obtained from this animal (Table 6). All founders and multiple offspring from MMTVLTR-TGFα lines TGF/1 and TGF/2, and MMTVLTR-c-erbB-2 lines ERB/1 to ERB/3 have been analysed in detail to the second (F2) generation. To date, 29 female MMTVLTR-TGFα transgenics and 34 female MMTVLTR-c-erbB-2 transgenics have been monitored for the development of mammary lesions that develop before 18 months of age.

Mammary Lesions in MMTVLTR-TGFα Transgenic Rats

MMTVLTR-TGFα female transgenics were fertile and able to nurse their young normally. Virgin mammary epithelium showed no growth abnormalities and did not express the transgene at levels detectable by Northern blotting of poly(A)-RNA or by immunocytochemistry. The MMTV-LTR promoter is usually activated by the hormones of pregnancy (Int. J. Cancer 52, 928–933,1992); therefore rats were subjected to repeated rounds of pregnancy and lactation to activate expression of the transgene. The most striking phenotype observed was the development of large, solid palpable lumps in the mammary glands during pregnancy. These lumps appeared in 41% of transgenic female rats in both transgenic lines after five or more pregnancies. In the most severe cases, lumps developed bilaterally in all the mammary glands. These lumps usually grew so large that the animals became moribund, necessitating culling. The lumps always appeared on day 10 or day 11 of pregnancy and invariably regressed the day before parturition, suggesting that they were severe hyperplasias rather than neoplasias. The animals were still able to lactate normally and nurse their young in the subsequent lactational period following regression of these lesions. However, the lumps usually reappeared with greater severity during subsequent pregnancies.

FIG. 7a–h shows the histology and immunocytochemistry of mammary lesions and tumours in MMTVLTR-TGFα transgenic rats.

Figure 7A:

FIG. 7a—Normal pregnant mammary gland from a non-transgenic female rat stained with haematoxylin and eosin (H&E).

Figure 7B:

FIG. 7b—Severe hyperplasia of the mammary gland at day 16 of pregnancy in a multiparous transgenic rat (H&E).

Figure 7C:
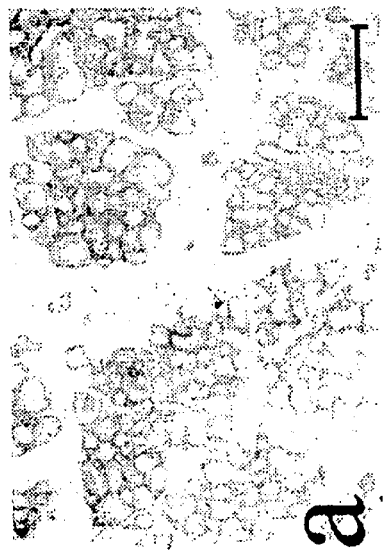

FIG. 7c—Hyperplastic mammary tissue from a multiparous transgenic rat stained with antiserum to TGFα. The majority of the epithelial cells stain moderately or strongly.

Figure 7D:

FIG. 7d—Mammary gland from a multiparous female transgenic rat 3 months after weaning from its previous litter. Note the persistence of hyperplastic lactating alveoli (hy) (H&E).

Figure 7E:

FIG. 7e—Normal regressed mammary gland from a non-transgenic female rat of the same strain and reproductive history as the rat in (d) above. Note the small condensed lobules (H&E).

Figure 7F:
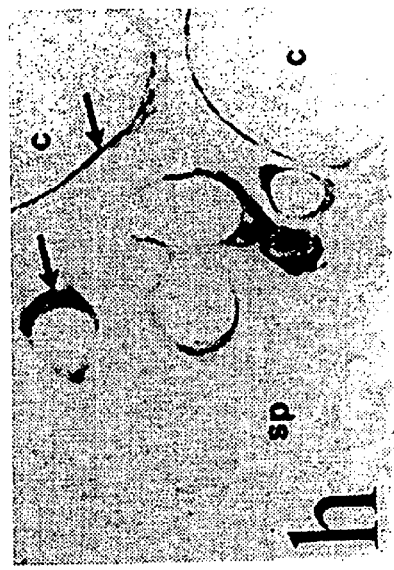

FIG. 7f—Mammary carcinoma with squamous metaplasia (sq) surrounding a cystic space (cy) and sebaceous gland-like elements (se) in a multiparous transgenic female rat (H&E).

Figure 7G:
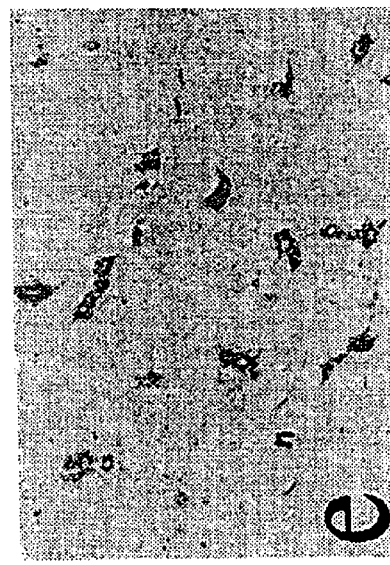

FIG. 7g—Fibroma in the mammary gland of a multiparous female transgenic rat stained with antiserum to TGFα. Note the strong staining of the stromal fibroblastic cell (arrows), whereas the ductal epithelial cells (ep) failed to stain.

Figure 7H:
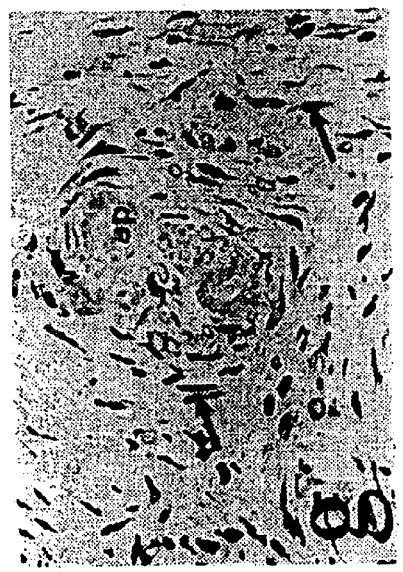

FIG. 7h—Mammary carcinoma with squamous metaplasia (sq) in a multiparous female transgenic rat stained with antiserum to TFGα. The anaplastic spindle cells (sp) that make up the majority of the tumour failed to stain, but the areas of squamous metaplasia (sq) surround the cystic spaces (c) stained intensely.

Magnification for a,b,d and e×58; Bar=200 μm. Magnification for c,f,g and h×230; Bar=50 μm.

When the sections were examined histologically, they were found to consist of solid masses of tissue resembling normal lactating mammary glands (FIGS. 7a,b). The hyperplastic mammary tissue compressed Wig around normal tissue such as skeletal muscle but did not invade it. The hyperplastic mammary tissue stained with antiserum to TGFα (FIG. 7c). Whole-mounts of mammary tissues from other pregnant transgenic female animals showed that the mammary tissue was always hyperplastic, in comparison with that from non-transgenic litter mates of comparable age and number of pregnancies. In transgenic females the fat pad became completely filled with proliferating mammary epithelium and individual lobules were impossible to distinguish because they merged together.

The mammary glands of transgenic female animals also failed to regress fully after lactation; dense, focal hyperplastic lobules with secretions persisted in these animals, even six months after their previous lactation (FIG. 7d). These hyperplastic lesions also stained with antiserum to TGFα. Involuted mammary glands from control litter-mates after comparable numbers of pregnancy and lactational cycles were very different, consisting of small, condensed ducts and alveoli with no evidence of lactation (FIG. 7e).

Tumours developed stochastically after a long latent period in multiparous females; by 18 months of age 8 of 29 (28%) of animals had developed tumours. These tumours were variable histologically; and included fibromas, benign papillary tumours with associated severed hyperplasia, ductal carcinoma in situ (DCIS) and carcinomas with squamous metaplasia (FIG. 7f). Transgene expression was variable; in fibromas the fibroblastic cells that made up the majority of the tumour stained strongly (FIG. 7g), whereas in DCIS and carcinomas expression of TGFα was either absent or non-uniform (FIG. 7h). However, strong expression of TGFα was always seen in adjacent hyperplastic breast tissue, when present, and in carcinomas where differentiation to squamous elements occurred (FIG. 7h).

Mammary Lesions in MMTVLTR-c-erbB-2 Transgenic Rats

MMTVLTR-c-erbB-2 transgenic females did not develop the severe pregnancy-dependent hyperplasias characteristic of the TGFα transgenics. Indeed, whole-mounted mammary glands of pregnant transgenic females did not reveal any evidence of hyperplasia. Transgene expression was not detectable in virgin females, and only just detectable in pregnant animals by immunocytochemistry and by Northern blotting of poly(A)-containing RNA. However, whole-mounted mammary glands from females at least six weeks after their previous lactation revealed focal areas of mild or moderate adenosis/hyperplasia.

FIGS. 8a–h show the histology and immunocytochemistry of mammary lesions and tumours in MMTVLTR-c-erbB-2 transgenic rats.

Figure 8A:
Figure 8B:
Figure 8C:
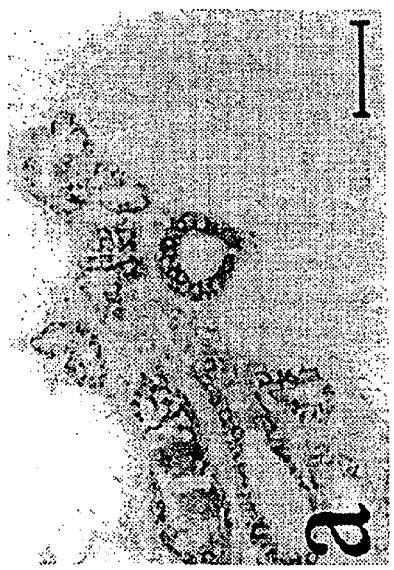
Figure 8D:
Figure 8E:
Figure 8F:
Figure 8G:
Figure 8H:
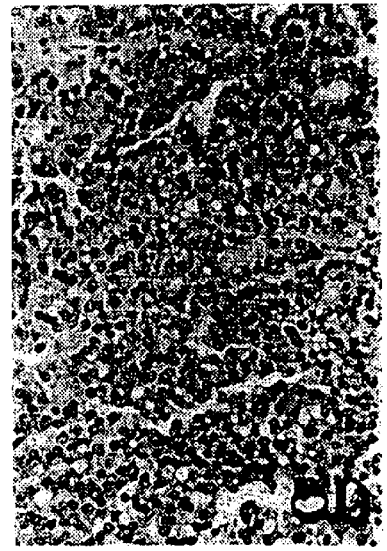

FIG. 8a—Regressed mammary gland from a multiparous female transgenic stained with antiserum to c-erbB-2. Note the weak membrane staining of the epithelial cells;

FIG. 8b—Area of fibroadenoma in a multiparous female transgenic rat (H&E);

FIG. 8c—Area of sclerosing adenosis in a multiparous female transgenic rat (H&E);

FIG. 8d—Fibroadenoma in a multiparous female transgenic rat stained with antiserum to c-erbB-2. The epithelia cells (ep) in the lesion stained moderately on their cell membranes;

FIG. 8e—Papillary tumour in a multiparous female transgenic rat. Note the intraductal epithelial proliferation and a large cystic space (cy) filled with secretory material;

FIG. 8f—Example of an area of ductal carcinoma in situ (DCIS) adjacent to a large cystic space (cy) in a multiparous female transgenic rat (H&E);

FIG. 8g Carcinoma in a multiparous female transgenic rat (H&E);

FIG. 8h The edge of the carcinoma shown in g above stained with antiserum to c-erbB-2. Note the strong membrane staining of the carcinoma cells (thick arrow), but the absence of staining in adjacent normal ducts (thin arrow).

Magnification for a,c,d,g and h×230; Bar=50 µm. Magnification for b,e and f×58; Bar=200 µm.

These mildly hyperplastic regions stained moderately or weakly on their plasma membrane with antiserum to c-erbB-2 (FIG. 8a), whereas cells in regressed, condensed alveoli in the same mammary gland failed to stain with antiserum to c-erbB-2. Although not as pronounced as in the MMTVLTR-TGFα transgenics, c-erbB-2 expression does appear to be correlated with retention of hyperplastic secretory alveoli.

Analysis of otherwise involuted mammary glands from multiparous transgenic females also revealed a variety or other pathologies. These included collections of thick ducts, which, when sectioned, appeared to be large cystic expansions, and multiple areas of focally dense tissue. When sectioned, these dense areas were usually found to be small fibroadenomas (FIG. 8b) or other benign lesions including sclerosing adenosis (FIG. 5c). These benign lesions are likely to be due to transgene expression and not arise spontaneously for three reasons. Firstly, they were multifocal. Secondly, they were observed very infrequently in mammary glands from control litter-mates of comparable age and reproductive history. Out of 20 control females only one area of mild fibroadenomatous change was found and areas of hyperplasia were not observed. Thirdly, both cystic expansions and fibroadenomas stained with antiserum to c-erbB-2 (FIG. 8d), whereas surrounding normal mammary tissue failed to stain.

As for the MMTVLTR-TGFα transgenics, tumours developed stochastically at low frequency after multiple pregnancies. These tumours included large fibroadenomas and histologically variable tumours with a papillary growth pattern, where the papillary epithelium lined cystic spaces in which dense secretions were present (FIG. 8e). Areas of DCIS were also present within these lesions (FIG. 8f) suggesting that a progression occurs from hyperplasia to papillary lesions and then to DCIS. To date 3 animals have developed DCIS and 2 animals have developed definite carcinomas. Although the carcinomas were well differentiated in comparison with most human breast carcinomas, they were poorly organized in comparison with the benign tumours and contained more malignant-looking cells with large, pleiomorphic nuclei (FIG. 8g). They were classified as definite carcinomas because they failed to stain with antisera to complex keratins and smooth muscle actin 1 indicating the absence of myoepithelial cells. Moreover, staining with antiserum to laminin revealed that basement membrane was either absent or very fragmented, indicating local invasion. Although cells in areas of DCIS stained weakly with c-erbB-2 antiserum, cells in carcinomas stained very strongly indeed on their membranes, whilst adjacent normal mammary ductal epithelium failed to stain (FIG. 8h).

Other Nonmammary Lesions in Transgenic Rats

FIGS. 9a–d show the immunocytochemistry of nonmammary tissue in transgenic rates.

Figure 9A:
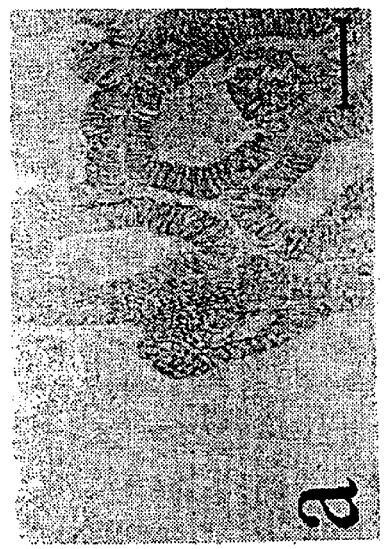
Figure 9B:
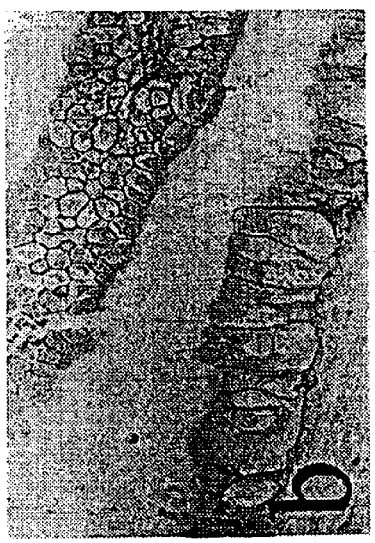
Figure 9C:
Figure 9D:
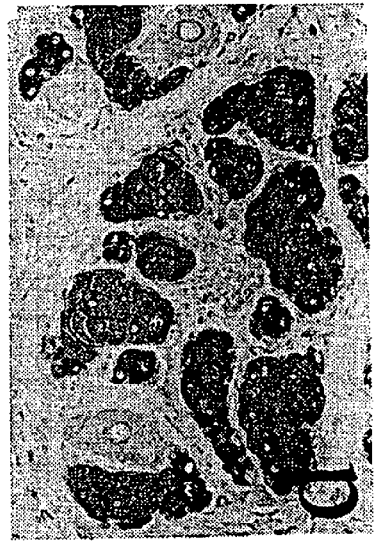

FIG. 9a—Seminal vesicle from a male ERB-1 transgenic rat stained with antiserum to c-erbB-2. The epithelial cells were stained weakly on their cell membranes;

FIG. 9b—Vas deferens from a male ERB-1 transgenic rat stained with antiserum to c-erbB-2. The epithelial cells were stained moderately on their cell membranes;

FIG. 9c—Salivary gland from a male ERB-1 transgenic rat stained with antiserum to C-erbB-2. Variable cytoplasmic staining was seen in the cells of the secretory acini;

FIG. 9d—Sebaceous gland hyperplasia in the dermis of the skin of a TGF-1 female transgenic rat stained with antiserum to TGFα. The sebaceous glands were stained intensely with this antiserum, whereas other structures failed to be stained.

Magnification×230; Bar=50 µm.

Although the MMTVLTR-TGFα and MMTVLTR-c-erbB-2 transgenes were also variably expressed in several other tissues, including the epithelial cells of the male reproductive tract (FIG. 9a,b), salivary glands (FIG. 9c) and areas of the kidneys and spleen, no apparent pathologies were observed in these tissues, with the notable exception of the salivary glands, where hyperplasia sometimes occurred in both MMTVLTR-TGFα and MMTVLTR-c-erbB-2 transgenic rat lines. These results suggest that either these other tissues are not susceptible to TGFα and c-erbB-2 induced carcinogenesis or that the level of transgene expression is not sufficient to induce a neoplastic phenotype in these tissues.

The only other striking phenotype of note was areas of hair loss, especially ventrally, in many of the MMTVLTR-TGFα transgenics. Transverse sections through the skin revealed areas of sebaceous gland hyperplasia. These hyperplastic sebaceous glands stained intensely with antiserum to TGFα, whereas the remainder of the dermis failed to stain and appeared to be normal (FIG. 9d). Dense hyperplastic mammary tissue was nearly always found in close proximity to these sebaceous gland hyperplasias, but it did not invade the sebaceous glands and hair follicles of the dermis. Therefore, sebaceous gland hyperplasia is most probably responsible for hair loss in these animals.

What is claimed is:

1. A neuronal cell line obtained from a transgenic rat which expresses a SV40tsA58 gene, the cells of which comprise:

(i) a conditional oncogene, transforming gene or immortalizing gene or a cell cycle affecting gene operably linked to (ii) a cell type specific promoter, in which the conditional oncogene, transforming gene or immortalizing gene or the cell cycle affecting gene is the SV40tsA58 gene, wherein the SV40tsA58 gene contains a thermolabile mutation of valine for alanine at position 438 in simian virus 40 T antigen gene and in which the cell type specific promoter is a human NF-L gene promoter.

2. A cell line as claimed in claim 1 having the ECACC Accession number 96092454.

3. A method of producing a transgenic rat expressing a SV40tsA58 gene, comprising:

(i) causing a female rat to super-ovulate by supplying her with a regular supply of Follicle Stimulating Hormone (FSH) prior to mating;

(ii) mating or artificially inseminating the female rat;

(iii) obtaining the resulting embryo from the female rat; and (iv) incorporating
   (i) a conditional oncogene, transforming gene or immortalizing gene or a cell cycle affecting gene operably linked to
   (ii) a cell specific promoter into the genome of the rat embryo in which the conditional oncogene, transforming gene or immortalizing gene or the cell cycle affecting gene is said SV40tsA58 gene, wherein the SV40tsA58 gene contains a thermolabile mutation of valine for alanine at position 438 in simian virus 40 T antigen gene and in which the cell type specific promoter is a human NF-L gene promoter.

4. A method as claimed in claim 3 wherein the FSH is supplied continuously.

5. A method as claimed in claim 3 or 4 wherein the supply of FSH is from 2 mg to 8 mg and the FSH is supplied over a 1 to 4 day period.

6. A transgenic rat which expresses a SV40tsA58 gene whose germ cells and somatic cells contain (i) a conditional oncogene, transforming gene or immortalizing gene or a cell cycle affecting gene operably linked to (ii) a cell type specific promoter as a result of chromosomal incorporation into the rat genome or into the genome of an ancestor of said rat in which the conditional oncogene, transforming gene or immortalizing gene or the cell cycle affecting gene is the SV40tsA58 gene, wherein the SV40tsA58 gene contains a thermolabile mutation of valine for alanine at position 438 in simian virus 40 T antigen gene and in which the cell type specific promoter is a human NF-L gene promoter.

7. A method of generating a cell line from a transgenic rat comprising a conditional oncogene, transforming gene or immortalizing gene or a cell cycle affecting gene operably linked to a cell specific promoter wherein the cell type specific promoter is a human NF-L gene promoter, the method comprising:

(i) maintaining the rat at restrictive conditions such that the conditional oncogene, transforming gene or immortalizing gene or the cell cycle affecting gene is a SV40tsA58 gene, wherein the SV40tsA58 gene contains a thermolabile mutation of valine for alanine at position 438 in simian virus 40 T antigen gene and is expressed in vivo, only in a tissue of interest and in an inactive form such that the cells thereof grow normally;

(ii) culturing said cells from the tissue of interest in vitro under permissive conditions such that the immortalizing function is activated, and (iii) subjecting the cells to non-permissive conditions so as to result in a cessation of growth and in differentiation.

8. A method as claimed in claim 7 wherein the conditional oncogene, transforming gene or immortalizing gene or the cell cycle affecting gene is a temperature sensitive gene.

9. A method as claimed in claim 7 or 8 wherein the permissive condition is a temperature of 33° C. and the restrictive condition is a temperature of 39° C.

10. A method of testing a material suspected of being a carcinogen, said method comprising administering said material to a rat produced according to the method of claim 5 or an ancestor thereof and detecting neoplasms as an indication of carcinogenicity.

11. A method of testing a material suspected of conferring protection against the development of neoplasms, said method comprising administering said material to a rat produced according to the method of claim 3 or an ancestor thereof and detecting a reduced incidence of development or neoplasms, compared to an untreated rat, as an indication of said protection.

* * * * *